United States Patent [19]
Alt

[11] Patent Number: 5,031,615
[45] Date of Patent: Jul. 16, 1991

[54] RATE RESPONSIVE CARDIAC PACEMAKER

[75] Inventor: Eckhard Alt, Ottobrunn, Fed. Rep. of Germany

[73] Assignee: Intermedics, Inc., Angleton, Tex.

[21] Appl. No.: 518,514

[22] Filed: May 2, 1990

[30] Foreign Application Priority Data

Sep. 12, 1986 [DE] Fed. Rep. of Germany ....... 3631155

[51] Int. Cl.$^5$ ............................................. A61N 1/00
[52] U.S. Cl. ............................................. 128/419 PG
[58] Field of Search ......... 128/419 PG, 419 P, 419 D

[56] References Cited

U.S. PATENT DOCUMENTS

| | | | |
|---|---|---|---|
| 4,428,378 | 1/1984 | Anderson et al. | 128/419 PG |
| 4,771,780 | 9/1988 | Sholder | 128/419 PG |
| 4,802,481 | 2/1988 | Schroeppel | 128/419 PG |

*Primary Examiner*—Francis Jaworski
*Assistant Examiner*—George Manuel
*Attorney, Agent, or Firm*—Leitner, Greene & Christensen

[57] ABSTRACT

An implantable activity-based cardiac pacemaker has a variable rate stimulus generator housed together with an accelermeter and associated circuitry within a case. The accelerometer is isolated from the case to detect forces of acceleration on the case while avoiding response to pressure on the case, and to generate an electrical signal representative of the magnitude of the accelerational forces. The accelerometer is integrated into hybrid electronic circuitry, such as a semiconductor chip, together with an electrical circuit which processes the signal generated by the accelerometer to vary the rate of the stimulus generator according to the magnitude of the signal. Either the accelerometer is configured as a mechanoelectrical transducer having a natural frequency response characteristic limited to a range below 4 Hz, or the electrical circuit itself includes an electrical filter having such a frequency response characteristic, so that the pacemaker is capable of distinguishing accelerational forces indicative of true physical exercise of the patient in whom the pacemaker is implanted.

20 Claims, 16 Drawing Sheets

RATE RESPONSIVE CARDIAC PACEMAKER

CROSS-REFERENCE TO RELATED APPLICATION

This application is a division of U.S. patent application Ser. No. 07/094,875, filed Sept. 10, 1987, now U.S. Pat. No. 4,926,863, issued May 22, 1990.

BACKGROUND OF THE INVENTION

1. Field of the Invention

The present invention relates generally to implantable cardiac pacemakers, and more particularly to an activity-sensing cardiac pacemaker which uses an integrated miniaturized accelerometer and related circuitry to detect patient activity and generate stimulating pulses at a physiologically appropriate rate depending on the intensity of the activity.

2. Relevant Background

Since the advent of the artificial implantable cardiac pacemaker, the aims of cardiac pacing have changed from the initial goal of simply providing a lower rate limit to prevent life-threatening asystoly, to the present-day broad objective of improving the overall quality of life of the pacemaker patient. Quality of life, in this context, pertains to the performance of the heart under widely varying metabolic and hemodynamic conditions. Patients with conventional single chamber pacemakers often lack adequate heart rate and cardiac output to sustain more than slight physical exertion, and consequently suffer severe limitations on activity and fitness. For patients with complete AV block and normal sinoatrial node activity, the dual-chamber pacemaker can restore an adequate adaptation of heart rate to exercise: but that solution serves only a relatively small portion of the pacemaker patient population, and such pacemakers are susceptible to disturbances.

As a result, numerous studies have been conducted over the years seeking to uncover parameters which act internal or external to the body for possible use in controlling pacemaker stimulation rate. The goal is to control the heart rate of a pacemaker patient in a manner similar to the intrinsic heart rate of a healthy person with a normal functioning heart, under various conditions of rest and exercise; which is to say, in a physiologically appropriate manner. Parameters for controlling the pacing rate heretofore studied and proposed in the patent and scientific literature include the QT time interval, which varies with the electrical depolarization and repolarization occurring during exercise (e.g., U.S. Pat. Nos. 4,201,219 and 4,228,803); respiration rate, and thoracic impedance changes arising from increased respiration with exercise, using external adhesive electrodes and an external pacemaker (e.g., U.S. Pat. No. 3,593,718 and European patent EP-A2-0135911); the blood pH balance (e.g., U.S. Pat. No. 4,009,721); the central venous oxygen saturation (e.g., U.S. Pat. Nos. 4,202,339 and 4,399,820); stroke volume (e.g., U.S. Pat. No. 4,535,774); nerve activity (e.g., German patent DE 28 09 091 and U.S. Pat. No. 4,201,219); and the central venous blood temperature (e.g., German patent DE OS 26 09 365).

Applicant's German Patent No. DE 84 19 439 and related U.S. application Ser. No. 747,111 ("the '111 application") discloses techniques for rate responsive pacing which utilize both absolute temperature values and relative temperature changes of the central venous blood of the patient under various physiological conditions, and which utilize separate algorithms defining heart rate as a function of blood temperature for states of rest and exercise, respectively, together with the decision rule for selecting which of the algorithms is appropriate at any given time.

Techniques for converting mechanical forces, accelerations and pressures into electrical energy and/or signals have also been proposed in the literature for use in biomedical technology. These techniques include the generation of electrical energy to power implanted devices from piezoelectric crystals and other mechano-electrical converters responsive to movement of the individual (e.g., U.S. Pat. Nos. 3,659,615 and 8,456,134); the use of a piezoelectric crystal embedded in silicone rubber and implanted in the pleural space between lung and ribs, to detect the respiratory rate for controlling the pacing rate (see Funke's publication in Journal Biomedizinische Technik 20, pp. 225-228 (1975)); the use of a piezoelectric sensor for measuring cardiac activity (U.S. Pat. No. 4,428,380); detecting patient activity with an implanted weighted cantilever arm piezoelectric crystal, and converting the output signal of the crystal into a drive signal for controlling the rate of a cardiac pacemaker (U.S. Pat. No. 4,140,132); and using the amplitude of a band-passed signal whose high frequency content increases with patient movement in an activity-responsive cardiac pacemaker (e.g., U.S. Pat. No. 4,428,378).

The aforementioned prior art parameters and techniques suffer various disadvantages when used in an effort to control pacemaker stimulation rate. For example, control according to the QT principle cannot distinguish emotional influences on QT interval changes from exercise-induced influences, which leads to sometimes unwanted and more pronounced emotionally-induced increases in the patient's heart rate. The change of respiratory rate with exercise varies widely between individuals, although less so with minute ventilation. Also, a person may voluntarily alter his or her respiratory rate without exercise and thereby adversely affect pacing rate. The pH level of the blood is not truly representative of patient metabolism because the significant changes toward acidity occur only at the higher levels of exercise. Similarly, changes of the central venous oxygen saturation are not a satisfactory indicator because a considerably greater decrease occurs at the beginning of exercise, even low work-load exercise, especially in those patients with limited cardiac output or tendency toward congestive heart failure, while continuing exercise may produce only slight further decreases. The stroke volume exhibits variations based on the position of the body, that is, according to whether the patient is sitting, lying or standing, which are independent of the level of exercise. The detection of patient activity by means of a neurodetector for the carotid nerve, for example, has serious limitations because of the nature of the surgery and the level of patient discomfort from this type of implant.

The detection of the activity- or motion-induced forces within or on the body by means of a piezoelectric crystal, a microphone or other mechanoelectrical transducer exhibits the desirable characteristic of a fast response to the onset of exercise, but has certain serious disadvantages including the deleterious effect of noise disturbances external to the body, such as from nearby operating machinery, or emanating within the body, such as from coughing, sneezing, laughing, or the like.

Accordingly, disturbances unrelated to exercise can affect the heart rate when accelerometer-type detection is utilized for control of the pacemaker stimulation rate.

It has been assumed in the prior art that the maximum acceleration values detected by an activity-controlled cardiac pacemaker in a patient undergoing exercise occur in the range of the resonant frequency of the major body compartments such as the thorax and the abdomen, i.e., approximately 10 Hz (e.g., see Proceedings of the European Symposium on Cardiac Pacing, editorial Grouz, pp. 786 to 790, Madrid, 1985). Thus, the prior art teaches that the maximum sensitivity should be in the range above 10 Hz (e.g., see also, Biomedizinische Technik, 4, pp. 79 to 84, 1986, and the aforementioned U.S. Pat. No. 4,428,378).

SUMMARY OF THE INVENTION

The present invention pertains to an aspect of the cardiac pacemaker disclosed in the aforementioned application Ser. No. 07/094,875, which reliably generates stimuli at rates adapted to the overall metabolic state of the patient. According to the invention, the pacing rate is adaptive to the level of physical exertion of the patient, closely corresponding to the heart rate of a normal healthy person under the same conditions of physical exertion. The pacemaker employs an accelerometer (activity or motion sensor) comprising a miniaturized mechanoelectrical converter or transducer formed in a semiconductor device to provide the small size and low power consumption, and which is adapted by its construction or by use of associated filter circuitry integral in the semiconductor device to pass signals in a frequency band selected to avoid increased rates of stimulation in response to false indications of exercise.

The preferred embodiment of the pacer in which the present invention is implemented also advantageously employs a second sensor for detecting a parameter complementary to acceleration, for dual sensor confirmation of metabolic state and selective contribution to stimulation rate. As used herein, the terminology "complementary parameter" is intended to mean any physiological or other detectable parameter of the body or acting outside the body, whose characteristics of sensitivity and specificity to physical exercise contrast with and enhance the corresponding characteristics of the activity sensor.

Known activity sensing pacers have the advantage of providing a fast response to the onset of exercise, but the disadvantage of a substantial inability to respond to the instantaneous metabolic level of exercise. In contrast, a parameter such as the central venous blood temperature, for example, responds less quickly to the onset of exercise, but is highly specific with respect to the metabolic level of exercise. Thus, the two parameters may be used in combination in a rate adaptive cardiac pacing system to complement each other by mutually supplying what the other lacks.

Based on considerable data obtained from healthy subject test volunteers and, as well, from testing of cardiac pacemaker patients, the applicant has found, using a primarily linear frequency sensor, that contrary to the teachings of the prior art the maximum forces occurring with physical activity are in the range of the frequency of the individual's steps in walking. The maximum amplitude is observed with the individual walking, whether on a level surface or up and down stairs, and with running, in the range of 1 to 4 Hz depending on the speed of the walking or running. The amplitude of these motion signals far exceeds signals from respiration and heart beat Further, the amplitude of these signals in the range of the response curve (the walking frequency), measured using a mechanoelectrical transducer which is configured for or used together with circuitry selective in this frequency range, has a direct and largely linear relation to the work performed. When the amplitudes of these low frequency signals (up to about 4 Hz) increase there is also an observable increase in the amplitudes of higher-frequency signals in the range above 4 Hz, but the latter are considerably smaller than those of the low-frequency range signals arising from physical activity.

Applicant's investigations indicate that the maximum amplitude activity-sensed signals occurring with exercise such as walking, climbing stairs, running and bicycling, take place with rhythmical motions of the body and are found in the low-frequency range below 4 Hz. Housework such as cleaning, vacuuming and the like also exhibits a maximum amplitude in the low-frequency range. In contrast, amplitude maxima in the higher-frequency range are the result of sudden spasmodic movements which do not represent true metabolic exercise, and the indicia of those movements are readily excluded by limiting detection to only the low-frequency content, which correlates well with the metabolic demand of the body in true exercise.

Noise detected from outside the body such as when the patient is in close proximity to operating machinery, or arising from within the body such as when the patient coughs, laughs, sneezes or strains, displays amplitudes in the higher-frequency range up to about tenfold the amplitudes of signals in the same range attributable to true physiological exercise. Thus, the noise signals tend to swam the activity-induced signals at the higher frequencies. Light knocks upon, bumps against or touching of the pacemaker are picked up by the internally mounted activity sensor and present impulse characteristics detected in the higher-frequency range, but are detected, if at all, with very low amplitudes in the low-frequency range up to 4 Hz. Also, because the duration of the pulse wave deriving from the propagation of the pulse with every heart beat is in the range of about 70 to 120 ms, it has an impulse characteristic with maximum amplitude in the higher-frequency range at about 10 Hz, despite the fact that the heart rate itself is in the range from 60 to 180 beats per minute (bpm) corresponding to a frequency of 1 to 8 Hz According to the applicant's measurements, riding in a car or on a bicycle on an uneven road surface produces some noise in the low-frequency range, but considerably below amplitude maxima detected within the higher-frequency range. In general, the ratio of activity-induced signal to disturbance-created noise in the low-frequency range is considerably better than in the higher-frequency range, and the low-frequency noise is readily discriminated from those signals representative of physical activity of the patient.

Advantageously, use of the low-frequency spectrum allows reliable detection of the amplitude maxima and minima with a relatively low sampling rate, in comparison to the high-frequency range, with an attendant saving of considerable energy. Since the energy capacity of an implanted pacemaker is limited, any saving of energy is important.

A further important aspect of the applicant's findings is that rate control may be achieved with an activity sensing pacemaker using relative changes of amplitude of the processed activity-induced signal, rather than the absolute signal values, for adjusting the stimulation rate. This is quite different from the teachings of the prior art, which invariably relies on the absolute values. Use of relative changes avoids false triggerings caused by ambient noise since a rate increase is dictated only when the value calculated from the signal exceeds a predetermined activity baseline. The rate increase is a function not only of whether the predetermined baseline value is exceeded, but also of the rate at the time this criterion is met. Thus, the relative extent of the increase will be less with increasing pacing rate, i.e., the specific amount of the increase will be smaller at the higher rates. Still, both the absolute amplitude and the relative change of amplitude of the activity signal may be evaluated to determine a stimulation rate increase, in part because of the relatively slower response of the second complementary parameter.

An embodiment of a rate responsive cardiac pacemaker in which the stimulation rate is controlled by detecting a second complementary parameter as well as by use of an activity sensor allows the control to be optimized to avoid prolonged false triggerings which might be encountered using the activity sensor alone. In a Fall 1985 presentation before the German, Austrian and Swiss Cardiological Society in Vienna, applicant discussed the possible use of a temperature sensor with an activity sensor of the type taught by the aforementioned U.S. Pat. No. 4,428,378 (see Zeitschrift fur Kardiologie, vol. 75, Abstract 69, 1985). An attendee of that presentation and his colleagues subsequently investigated whether the central venous blood temperature is a suitable measurable variable for use in combination with the specific activity control according to the latter patent (see Herzschrittmacher 6:64 to 67, 1986).

The preferred embodiment in which the present invention is implemented goes considerably beyond the mere use of plural parameters in a pacemaker. Rather, in one of its aspects, the complementary parameter is used to limit a noise-related false triggering of a rate increase by a relative change in the signal level of the mechanoelectrical transducer, and the output signal of the transducer is used to determine whether an increase in the stimulation rate attributable to the value of the complementary parameter is appropriate. For example, if venous blood temperature is the complementary parameter, fever may be detected (or confirmed) in the absence of an activity (motion) signal from the transducer, and the stimulation rate increase held to an appropriate lower value. That is, the new rate may be based on the signal representative of the measured complementary parameter when the absolute signal level of the activity transducer is below a predetermined minimum. Absence of motion dictates not only an absolute rate, but a minimum rate determined by the state of the complementary parameter.

After physical exercise, the stimulation rate of the preferred embodiment is decreased to a quiescent base rate (resting rate) according to a fall-back program (i.e., a rate reduction routine) as a function of the drops of the signals from both sensors. However, a decrease in stimulation rate to this base rate may be inhibited so long as the processed absolute signal amplitude of the activity sensor exceeds a predetermined level indicative of body activity. Thus, rate control is provided using the low frequency band and the relative change of the transducer signal amplitude in that band; and the absolute signal amplitude of the low-frequency processed transducer output allows detecting absence of motion for rate control according to a baseline characteristic relating heart rate to the second parameter, or detecting the presence of motion for suppression of a rate fall-back program. The mechanoelectrical transducer may thereby provide fast response for rate control at the onset of exercise and change of the workload, a shift to a resting baseline control by the complementary parameter in the absence of an activity-induced signal, and prevent or limit rate reduction in the presence of an activity-induced signal characteristic of exercise.

A feature of the preferred embodiment is that a new baseline or threshold level for activity is established according to the specific inertia criteria or characteristics of the complementary parameter, which may be one of the exemplary parameters mentioned above or the natural sinus node activity in a dual chamber pacemaker. After a certain time interval (e.g., a few minutes) with no confirmation of the transducer signal by the complementary parameter sensor signal, the then-current activity signal amplitude is assumed to be the new baseline, zero or quiescent value of activity. Thereby, a prolonged improper rate increase from false triggering of the activity sensor is avoided even in a noisy environment.

If the transducer output signal is zero or less than a predetermined minimum absolute amplitude, and the detected value of the complementary parameter is increasing, the preferred pacer embodiment will initiate a fall-back program to return the stimulation rate toward a predetermined base or resting rate. Such circumstances indicate that the patient is not undergoing physical exertion, and that it is appropriate at this point to reduce the stimulation rate to the base rate. This feature may be utilized to discriminate and halt reentry tachycardias in atrial P-wave triggered DDD pacemakers.

Protection is provided against prolonged improper rate increases from false triggerings of the activity transducer, and against prolonged rate increases attributable solely to the sensed value of the complementary parameter. Furthermore, the extent of rate control accorded to that complementary second parameter can differ according to the nature of the signal (or lack thereof) deriving from the activity transducer.

According to a feature of the invention, the mechanoelectrical transducer is a piezoelectric, piezoresistive or piezocapacitive sensor of the semiconductor type, which is integrated with signal processing circuitry in a silicon chip. The integrated circuit is manufactured using conventional semiconductor process technology. By fabricating the sensor with appropriate geometrical configuration, the sensor itself provides the desired frequency bandpass characteristics to capture the proper signal. For example, the transducer may comprise a vibratory cantilever arm of material and length selected to provide it with the desired resonant frequency.

The present invention provides an activity-sensing cardiac pacemaker for implantation in a patient, with a case housing at least a portion of the pacemaker, and activity sensor means situated within the case for detecting movements of the patient. The activity sensor means includes miniaturized accelerometer means integrated within a semiconductor device to distinguish between movements of the type attributable to physical exercise of the patient and movements of the type produced by spasmodic reaction to internal and external influences on the patient, for generating an electrical signal level representative of patient movement attributable to physical exercise. An adjustable rate pulse generator within the case supplies pulses to implanted pacemaker leads to stimulate the patient's heart, and is responsive to the signal level of the accelerometer means to adjust the plus rate to stimulate the patient's heart at a rate which is physiologically appropriate to the level of physical exercise of the patient.

BRIEF DESCRIPTION OF THE DRAWINGS

The above and other objects, aspects, features and advantages of the present invention will become more apparent from a consideration of the ensuing detailed description of a presently preferred embodiment thereof, taken in conjunction with the accompanying drawings, in which.

DETAILED DESCRIPTION OF THE PREFERRED EMBODIMENT

Figure 1:
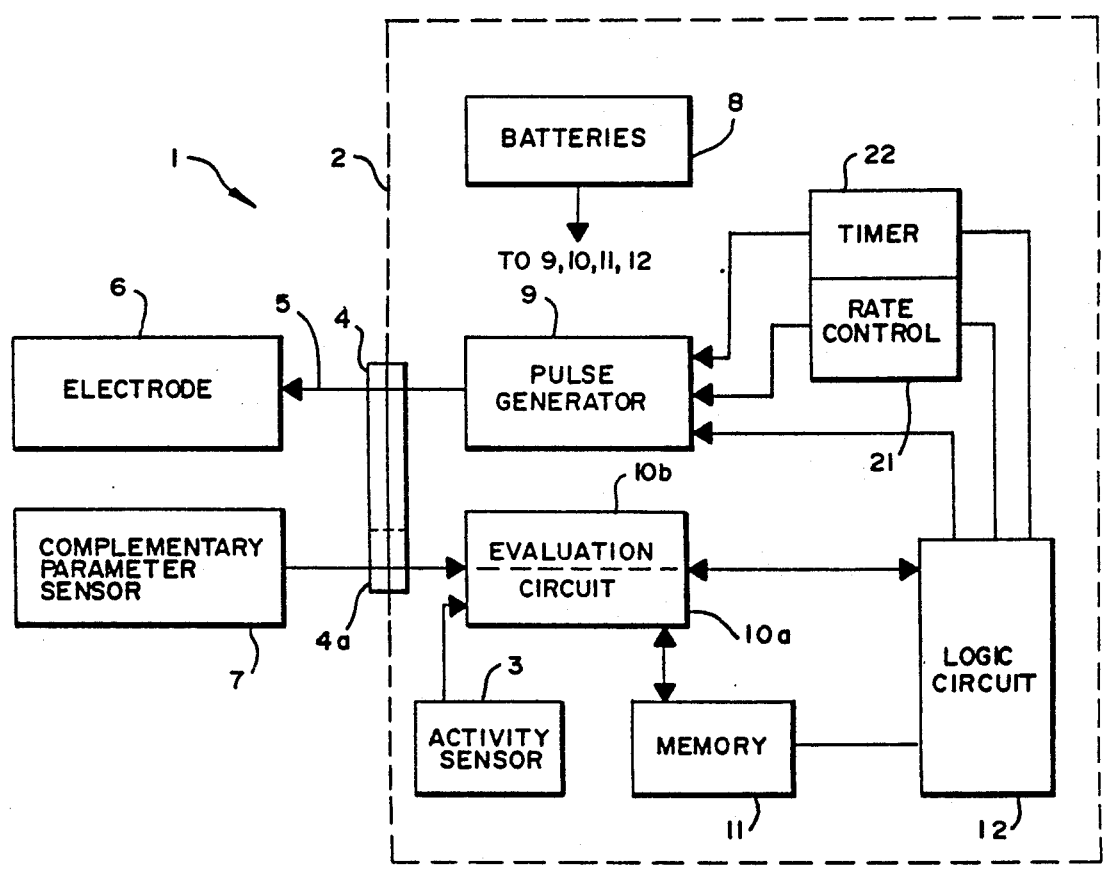
FIG. 1 is a block diagram of a cardiac pacemaker according to the invention.

Referring now to FIG. 1, a cardiac pacemaker 1 includes a case 2 in which the various components are housed, including evaluation circuitry 10a and activity sensor (mechanoelectrical transducer) 3. The circuitry within case 2 is connected via a conventional connector 4 to a pacing lead 5 with a stimulating electrode tip 6. The pacing lead(s), for example, is of the endocardial catheter type for insertion intravenously to position the stimulating electrode(s) relative to excitable myocardial tissue in the appropriate chamber(s) of the right side of the patient's heart. The pacemaker may be arranged in conventional fashion for unipolar or bipolar stimulation, and may include known sensing electrode(s) and processing circuitry therefor as well.

A second sensor 7 electrically connected to the pacemaker circuitry via a suitable connector 4a, for example, is provided for detecting a second complementary physiological parameter, such as the natural atrial rate, the QT interval, the pH value of the blood, the blood oxygen saturation, the respiration, the central venous blood temperature, or other recognized parameter of or acting on the body, whose value is related to heart rate. In the preferred embodiment, the central venous blood temperature is chosen as the complementary second parameter and will be referred to in that respect throughout the ensuing description, but the invention is not limited to the use of blood temperature. By using blood temperature as the complementary parameter all of the teachings of the '111 application are readily and advantageously employed. Sensor 7 in this embodiment, therefore, may be a thermistor or other suitable temperature sensing element located in the pacing lead 5, in the manner described in the '111 application, for sensing the blood temperature in the atrium or ventricle of the right side of the patient's heart.

The implanted pacemaker case 2 further houses a battery 8; a pulse generator 9, whose pulse rate is controllably variable, for generating the stimulating pulses to be delivered to pacing electrode 6 for stimulating the patient's heart; evaluation circuits 10a, 10b for processing and evaluating the signals deriving from activity sensor 3 and temperature sensor 7, respectively; a memory Il for storing data, such as programmed values in conjunction with a conventional external programmer and other data of the type to be described, including a baseline curve and exercise curves (algorithms) representing heart rate as a function of blood temperature, as set forth in the '111 application; and a logic circuit 12 for controlling the sampling of signals from the sensor and the rate of the pulse generator.

Figure 2A:
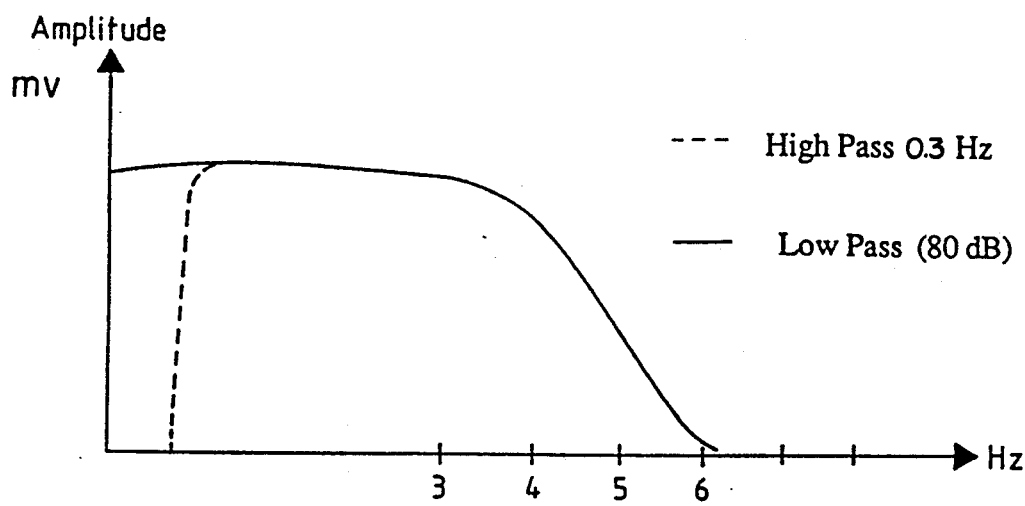
FIG. 2a is a schematic diagram of a frequency spectrum of the low-pass (band-pass) signals of a mechanoelectrical transducer (activity sensor) used in the pacemaker of FIG. 1.

Activity sensor 3 is a small mechanoelectrical transducer, preferably of a type mentioned above, which is either fabricated in a conventional manner to provide a inherent frequency band characteristic selected according to the teachings of the present invention, or is coupled to a filter circuit to pass signals in that selected band. The frequency spectrum of the band-passed signals from activity sensor 8 is represented in FIG. 2a, with low pass filtering producing a rapid drop-off at frequencies exceeding 4 Hz, and with high pass filtering to eliminate DC and frequencies below the 0.3 Hz level.

Figure 2B:
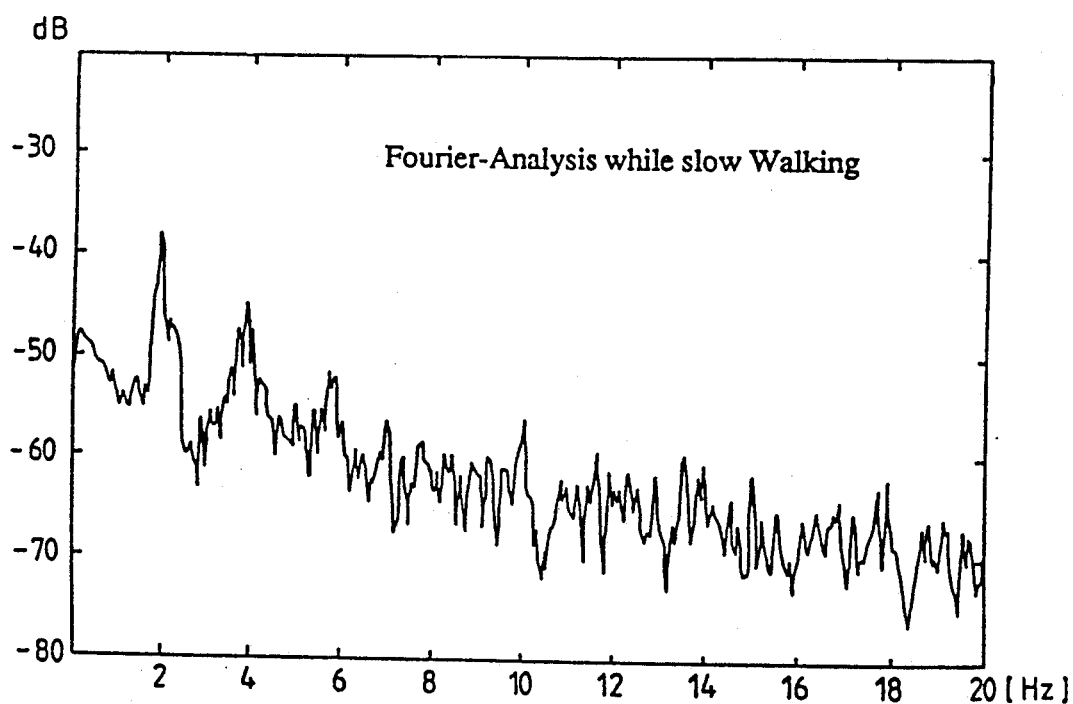
FIG. 2b shows a Fourier analysis with respect to the frequency and amplitude of the signals from the mechanoelectrical transducer for the activity of slow walking.
Figure 2C:
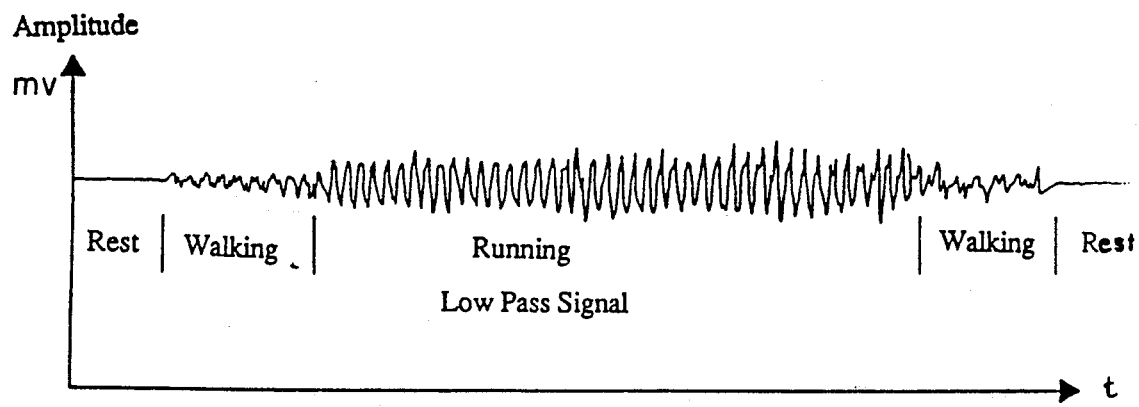
FIGS. 2c through 2f each show frequency and amplitude spectra for different types of activity and disturbances.
Figure 2D:
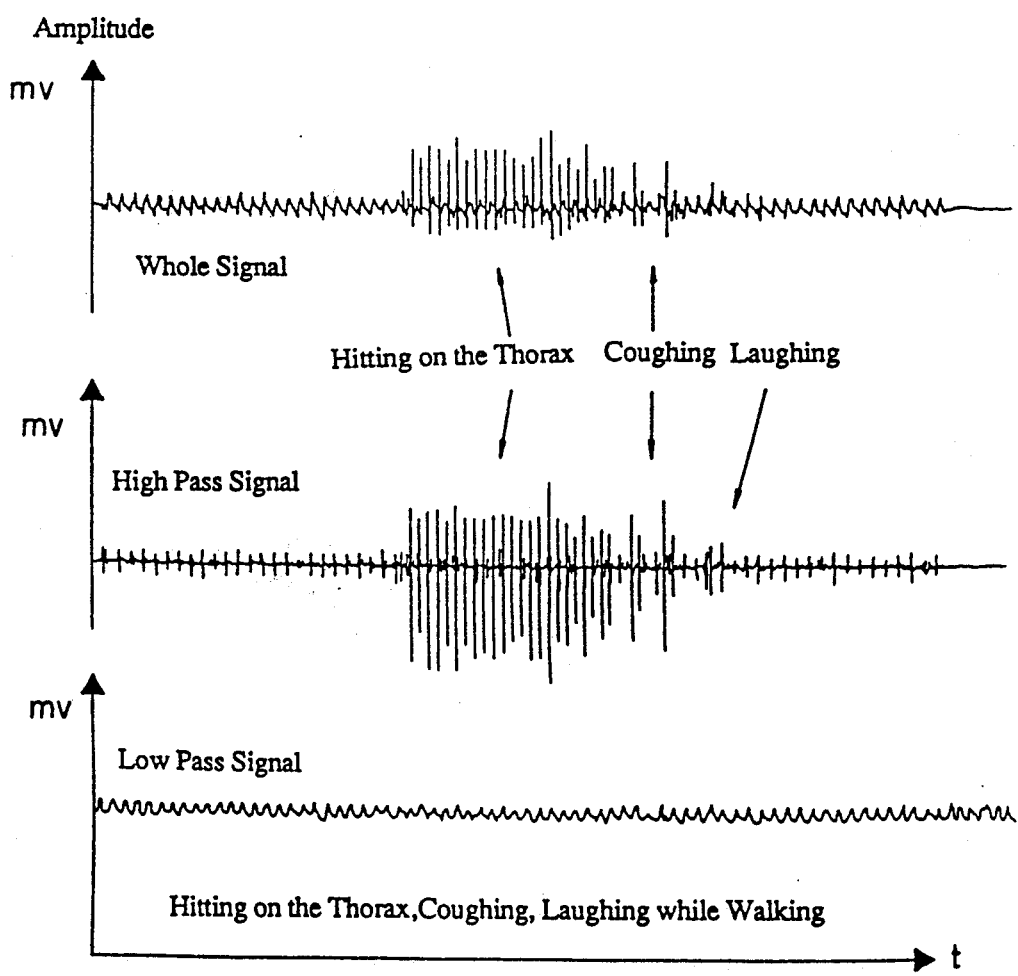

In FIGS. 2b to 2f, the output signals of sensor 3 are analyzed for several different types of activity. FIG. 2b is a Fourier analysis of the processed signals of the activity sensor showing frequency measured in Hz and amplitude measured in dB, detected in a slowly walking test subject. FIG. 2c charts the amplitude relative to time of the low-pass signal (i.e., in the band from about 0.3 Hz to 4 Hz) processed from the activity sensor for successive intervals of rest, walking, running, walking and return to rest by the subject. FIG. 2d illustrates, in three separate charts, the unfiltered complete output signal of the activity sensor (upper chart), the high-pass portion (i.e., above the selected band) of the signal (middle chart), and the low-pass portion of the signal (lower chart), detected from a walking subject in which successive intervals of noise are encountered by touching of the pacemaker, coughing and laughing by the subject.

As will be observed from FIG. 2b, the frequency spectrum for movement of the subject by foot indicates a clear maximum amplitude at a frequency of approximately 2 Hz: and significantly declining signal amplitudes in the range exceeding 4 Hz. FIG. 2c shows an increase in the amplitude of the low-pass activity signal with increasing exercise as the subject goes from walking to running, and an amplitude decrease as the subject returns to walking and ultimately to a state of rest. FIG. 2d clearly demonstrates that the low-pass activity signal is virtually unencumbered by the noise generated from impact on the pulse generator case, coughing, laughing or the like, the signal indicative of walking being cleanly detected. In contrast, the higher frequency range is significantly affected by that noise, so much so that the signal representative of the walking is buried in the noise.

Figure 2E:
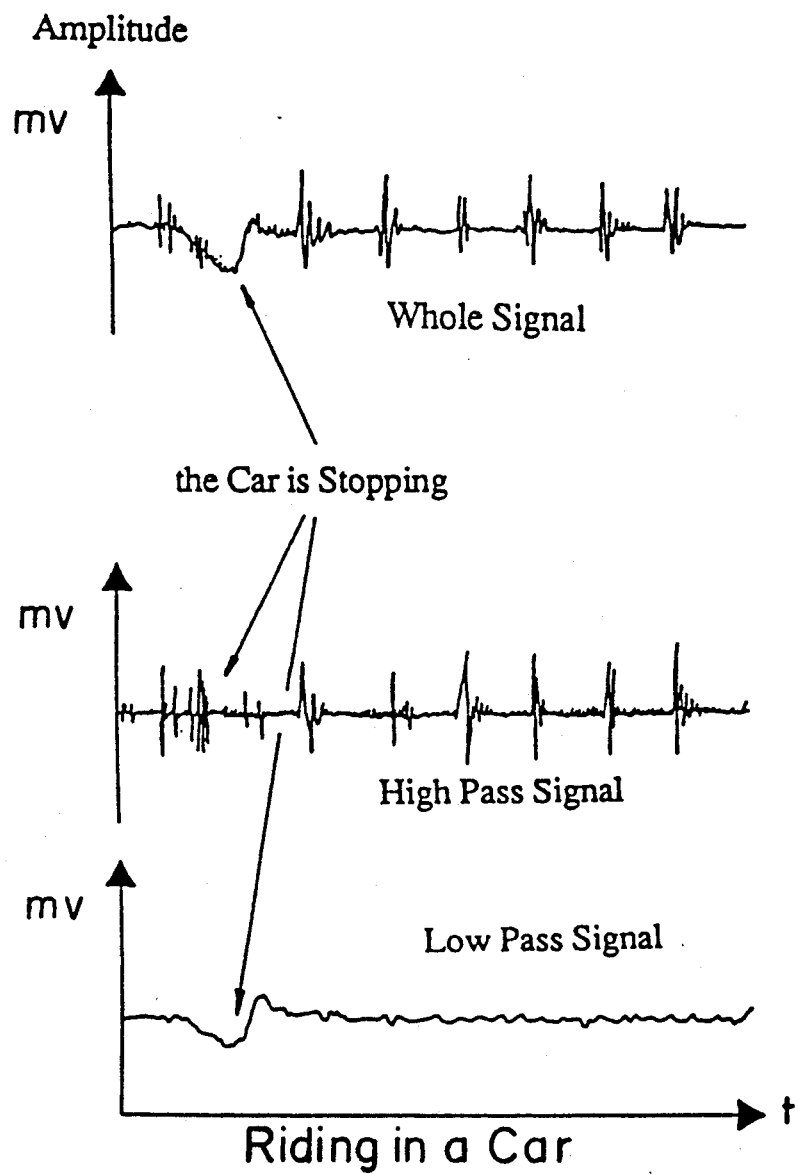
Figure 2F:
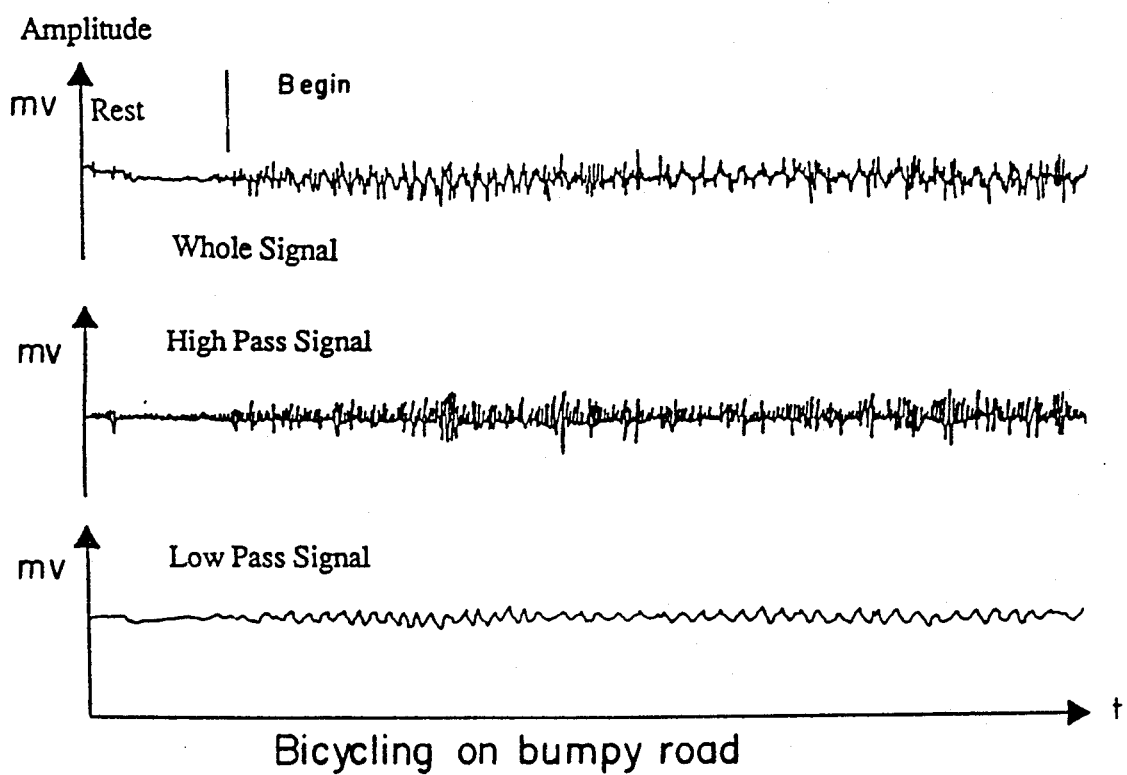

FIGS. 2e and 2f show the signal amplitudes over time for the entire frequency spectrum (upper chart), the high-pass portion (middle chart), and the low-pass portion (lower chart), when the subject is riding in a car and bicycling on an uneven road, respectively. Here again, it is abundantly clear from the test results that the frequency range below 4 Hz provides an indication of true activity, virtually uninfluenced by any noise peaks. In FIG. 2e, the higher frequency range is replete with noise including spikes at the resonance of the moving car. In FIG. 2f, the noise is also pronounced at the higher frequencies, with a more homogeneous noise distribution attributable to the uneven road surface traversed by the bicycle. In both cases the true activity signal is masked. It will thus be apparent, contrary to the teachings of the prior art, that processing only the lower frequency band of the activity sensor output provides a considerably more accurate indication of true exercise while avoiding the many false triggerings of rate increases by the pacemaker which can result from noise detected in the higher frequency band.

Figure 3:
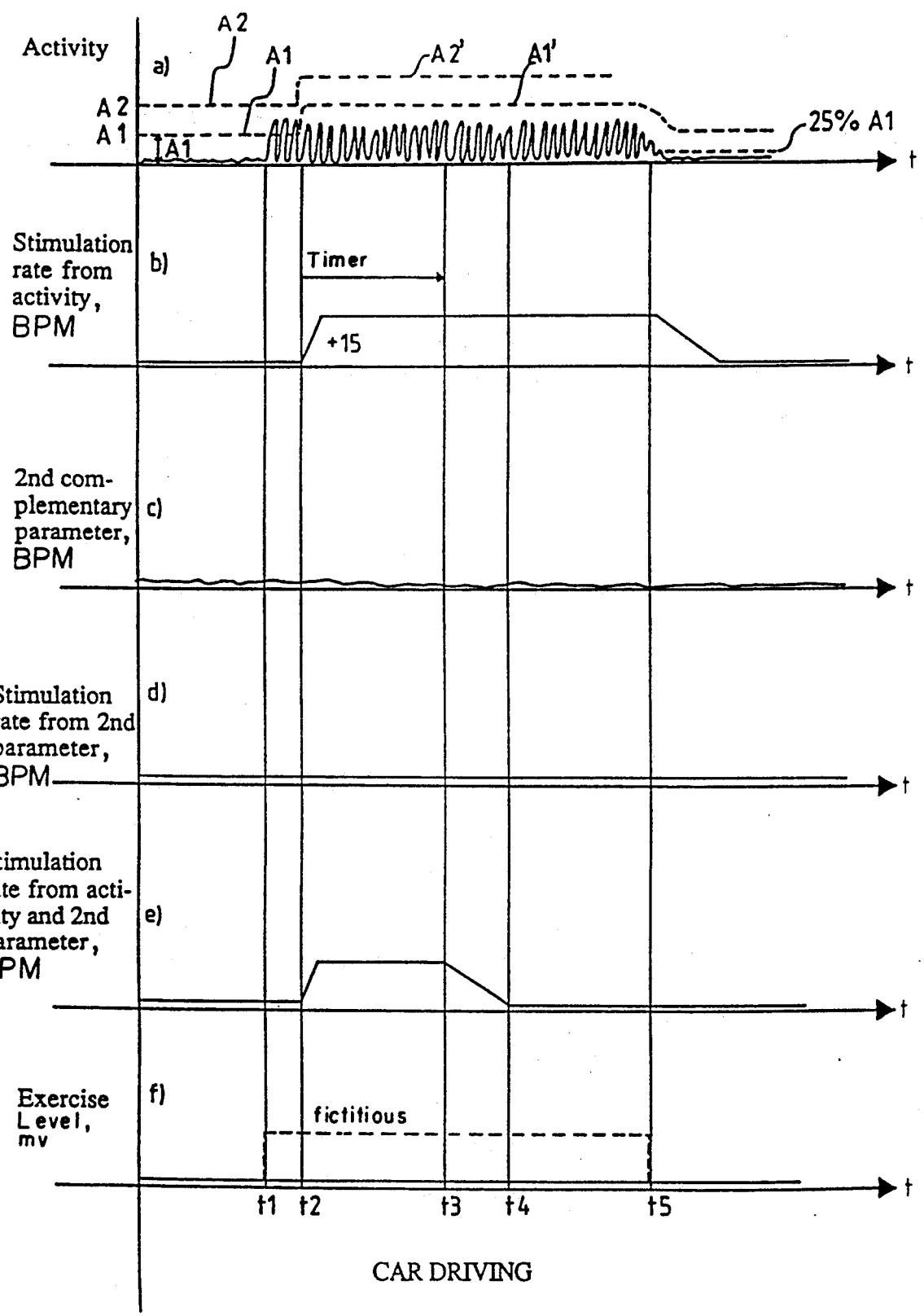
FIGS. 3 to 7 and 10 are diagrams of signals developed in the pacemaker of FIG. 1 for indicated types of activity.

FIG. 3 shows the behavior of the cardiac pacemaker of the present invention when subjected to a false triggering attributable to noise, encountered while the patient is riding in a car for example. Part (f) of FIG. 8 and also of similarly formatted FIGS. 4 to 7 indicates the nature of the exercise workload. In each of these FIGS. the time scale is partly compressed and does not correspond to actual time. For example, the interval between times t1 and t2 is typically only two or three seconds in duration, whereas at least some of the subsequent time intervals may be of several minutes duration each.

In the example of FIG. 3, the "exercise" is fictitious, with the signal detection resulting strictly from noise. Part (a) shows the processed output of activity sensor 3 for the aforesaid low frequency band. Up to time t1 the pacemaker patient is merely sitting in the stationary car; hence, no signal or only small signal variations (attributable to slight movement of the patient in the idling vehicle, for example) are detected. At t1, the car starts moving and a higher signal level is detected. It is important to observe that the signal amplitude is exaggerated for the sake of explaining this example; as was observed in FIG. 2e, the low frequency band is quite effective to filter disturbances arising from the moving car.

Processing of the signal after filtering may be accomplished in different ways. For example, the evaluation circuit 10a may be adapted to operate on the band-passed signal over successive blocks of time of, say, three seconds each. The difference between the maximum and minimum signal amplitudes is calculated for samples taken at predetermined intervals of, say, 300 milliseconds each. The calculated amplitude difference is then added to the calculation for the previous sample for all X samples of Block 1 (i.e., the first three second period, in this example), and the value obtained is then averaged for Block 1 by dividing that value by the number of samples taken. If the difference between that average and the average for Block 2 (i.e., the next three second period) exceeds a predetermined activity baseline related to units of gravity, and if this is confirmed over the next few blocks of time, it is indicative of activity or of a significant increase of activity (additional activity). This is the post-filtered signal processing technique employed in the preferred embodiment of the invention, although various other suitable techniques will be apparent to the skilled artisan. In this manner, random or spasmodic movements which might otherwise be regarded as exercise can be disregarded.

Referring again to part (a) of FIG. 3, the jump in the filtered activity signal occurs at time t1 (or an instant later depending on the response time of the activity sensor). The processed data is compared with predetermined baseline or threshold values of activity A1, A2, and so forth, each of which may be freely programmable and stored in the memory 11 (which, incidentally, was also used to store sampled values for the aforementioned data processing). The initial activity thresholds may be selected according to the particular patient and the type of accelerometer (activity sensor) employed for the pacemaker. By way of example, 0.15 g (unit of gravity) was deemed an acceptable level indicative of patient activity for one test subject, using an embodiment of an activity sensor for which that level of movement produced a signal level of about 60 millivolts.

If the previously described processing calculation exceeds the first threshold A1, the logic circuit 12 controllably initiates an increase in the rate at which stimulating pulses are generated by the pulse generator 9 by an amount of, say, 15 pulses per minute (ppm, equivalent to bpm). If the second threshold A2 were exceeded at t1, the pulse rate would be increased by a greater amount, say, 26 ppm. This rate increase is accomplished as follows. Logic circuit 12 responds to threshold A1 having been exceeded at t1, by initiating at t2 a preset timing function of a rate controller 21 to which it is connected within housing 2, to increase the pacing rate of the pulse generator 9 by 15 bpm. This timing function produces a predetermined transition to the higher pacing rate, as represented in part (b) of FIG. 3. If there is no further significant change in the processed signal calculations as described above, this increased stimulation rate will continue in effect. At the same time that the rate increase is initiated, the exceeded activity threshold A1 is designated as the new activity baseline, and a higher activity threshold A1' (and A2', etc.) is set from which to determine additional activity, as will be further explained presently.

At any time that the absolute amplitude of the activity signal drops to 25% of the activity threshold which was exceeded to cause the rate increase, the logic circuit initiates a fall-back program through another timing function of rate controller 21 to gradually reduce the stimulation rate of the pulse generator back to a preprogrammed base rate. As shown in FIG. 3(f), the car comes to a stop at t5. The absolute level of the detected activity signal drops to 25% of activity threshold A1 an instant thereafter (FIG. 3(a)), and the pacing rate is decreased commencing at that time (FIG. 3(b)).

However, the present invention also serves to avoid prolonged rate increases from false triggerings of the pacemaker as a result of high levels of noise in the filtered output of the activity sensor, even in those instances where the noise is present in the low frequency band and is not rejected by the aforementioned signal processing calculations. To that end, the logic circuit 12 actuates a timer 22 at t2, coincident with the triggering of the rate increase via rate controller 21, to commence timing a predetermined period (FIG. 3(b)) whose duration is preset according to the response time of the selected second complementary parameter to the onset of exercise or to abrupt changes in level of exercise. In the presently preferred embodiment, where blood temperature is the complementary parameter, the period of timer 22 may be set, for example, at two to three minutes. In general, sensors of the physiological parameters mentioned earlier herein ar less sensitive to the onset of exercise than an activity sensor, but as previously noted herein, each of these other parameters is a suitable complementary parameter to acceleration because of their greater specificity in indicating the varying level of ongoing exercise. If one of these other parameters were used in place of blood temperature, the timer 22 period would be set accordingly. The duration of the timer period is important because if, during that period, the stimulation rate dictated by the second complementary parameter exceeds the rate dictated by the activity signal, the latter relinquishes and the former assumes control of the stimulation rate. On the other hand, if the second complementary parameter fails to assume such control, this constitutes a lack of confirmation of the activity signal and an indication of no true activity or of insufficient activity to warrant the rate increase. Accordingly, in the latter circumstance the logic circuit 12 actuates the rate controller 21 to initiate a rate reduction routine (fallback program) at the end of the period of timer 22.

The blood temperature measured by thermistor 7 over the timer period is represented in FIG. 3(c). The stimulation rate is calculated from the measured blood temperature as described in the '111 application, and is represented in FIG. 3(d). Of course, in this example the "exercise" is fictitious, and consequently the temporal increase, if any, in the blood temperature would be insufficient to produce a stimulation rate other than is commensurate with the baseline resting curve. In fact, there is no substantial change in the blood temperature according to FIG. 3(c), and therefore virtually no change in the rate determined from the blood temperature as shown in FIG. 3(d). Hence, at time t3, when the timer period expires, logic circuit 12 initiates the rate fallback program of rate controller 21 to gradually reduce the stimulation rate of pulse generator 9 to the programmed base rate at t4. This assures that the patient will not be subjected to improper rate increases as a result of false triggerings for more than the relatively short duration of the timer period, rather than experiencing a prolonged rate increase, for example, over a four hour car ride.

If the evaluation of the filtered activity sensor output indicates a reduction in the averaged maxima and minima of the signal by 75% or more to a value of 25% or less of the activity threshold which has just been exceeded, it is assumed that exercise has ceased. At that point, the logic circuit will initiate the fallback program of rate controller 21 to return the pulse rate of pulse generator 9 to the base rate. The various threshold values and the criterion of reduction of below last-exceeded activity threshold may be selected (programmed) according to the individual patient.

The arrangement of the diagrams in FIG. 3 is repeated in FIGS. 4 to 7, inclusive. In each FIG.: part (a) represents the filtered low-frequency band output signal of activity sensor 3; part (b) illustrates the stimulation rate (heart rate) attributable to the signal of part (a); part (c) shows the value or the signal representative thereof for the second complementary parameter—in the presently preferred embodiment, the blood temperature detected by sensor 7 part (d) represents the stimulation rate determined according to the value shown in part (c); part (e) shows the effective stimulation rate derived from both parameters (activity and blood temperature); and part (f) schematically represents the exercise level or workload.

Figure 4:
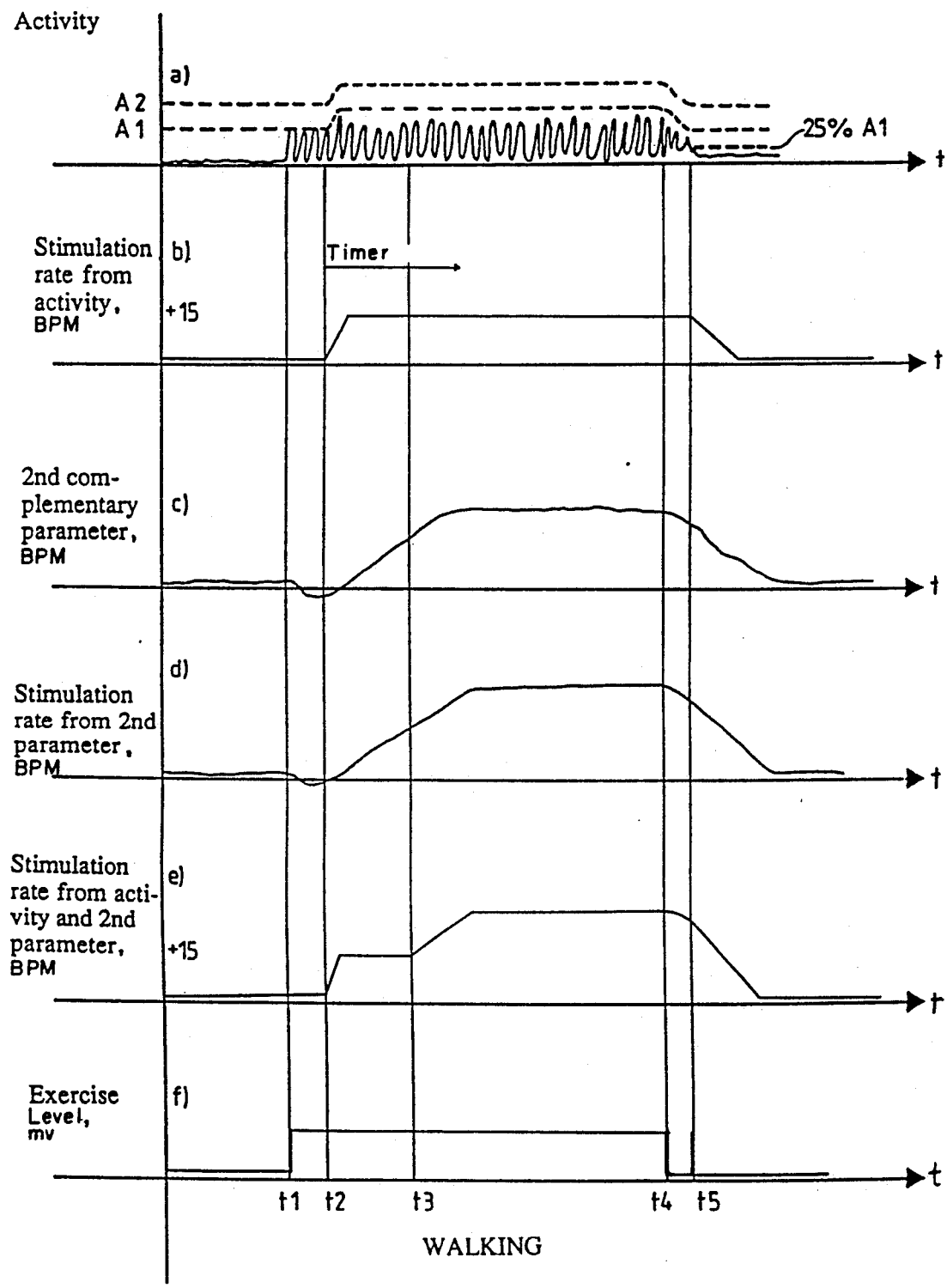

FIG. 4 is a diagram representing the behavior of the pacemaker for a patient who commences walking for a period of time and then returns to a state of rest. Part (f) indicates that the exercise starts at time t1, and is thereupon detected by the activity sensor (part (a)). The filtered signal amplitude is processed by the evaluation circuit 10a and, after a brief interval, the calculated value is found to exceed activity threshold A1. Accordingly, pulse generator 9 is adjusted via rate controller 21, under the control of logic circuit 12, to increase the pacing rate by 15 bpm commencing at time t2, as shown in FIG. 4(b). At time t4, the exercise ceases and this is recognized at time t5, when the calculated value of the processed activity signal has dropped to 25% of the activity threshold A1. In those circumstances, if the rate control were based strictly on the output of the activity sensor the stimulation rate would be reduced gradually toward the programmed base rate under the rate reduction routine of rate controller 21, as was described in connection with FIG. 3.

Here however, the blood temperature increases with the exercise, after the characteristic dip at the onset thereof, and continues to increase until it reaches a steady state value FIG. 4(c). At time t3 before the timer 22 period has expired, the stimulation rate determined according to blood temperature exceeds the rate determined from the activity signal (FIG. 4(d)). Thereupon, the detected blood temperature becomes the rate-determining parameter and the stimulation rate is increased according to the blood temperature (FIG. 4(e)), under the control of the logic circuit and the rate controller. This situation continues, with rate determined by blood temperature, until the exercise ends at t4. The blood temperature begins dropping off rapidly (FIG. 4(c)), and, with it, the stimulation rate begins to decline (FIG. 4(d) and (e)). At time t5, the value calculation from the processed activity signal drops to 25% of activity threshold A1, instituting the fallback program according to that parameter as well, and the combined stimulation continues its decline to the base rate (FIG. 4(e)).

Figure 5:
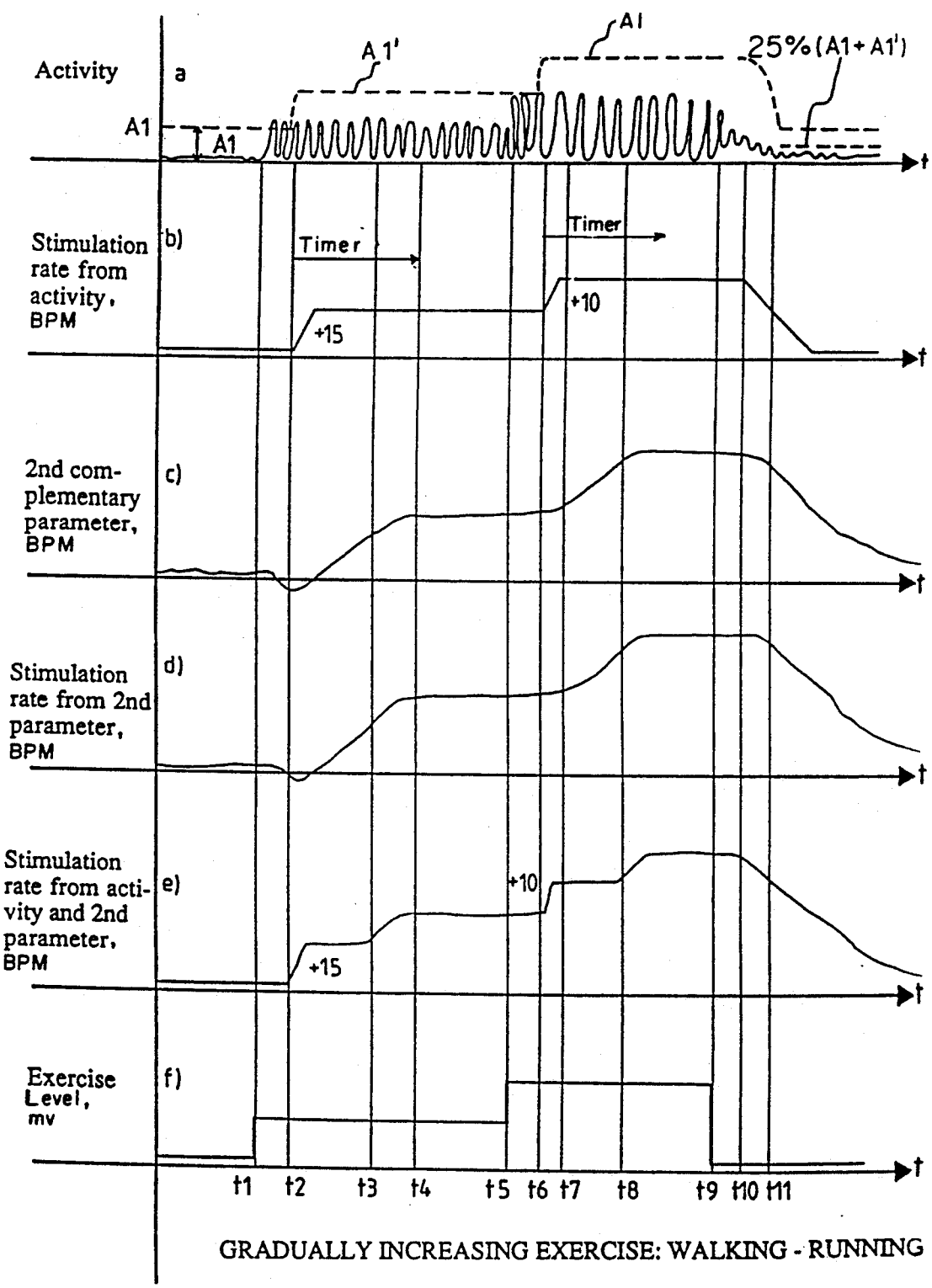

FIG. 5 illustrates the behavior of a pacemaker according to the invention when the patient undergoes gradual increases of exercise, in the stepped manner shown in part (f). Initially, with the patient at rest, the pacing rate is maintained at the base rate. At t1, the patient begins walking, and, in response to detection of the rhythmical movement, the activity sensor generates a signal which is filtered in the frequency band of interest as shown in part (a). The signal is then processed to calculate the average difference between amplitude maxima and minima for a sequence of samples over the selected time interval, as described earlier. At time t2, the evaluation circuit determines that the calculated average exceeds activity threshold A1, and, in response, logic circuit 12 increases the stimulation rate by 15 bpm via rate controller 21, and also actuates timer 22 (FIG. 5(b)). The exceeded threshold A1 is thereupon stored in the memory 11 as the new baseline for activity, and a new higher activity threshold A1' is established (FIG. 5(a)). The latter is also stored in the memory, along with all other data to be utilized or operated on including base stimulation rate and the current increased rate. As a consequence of the establishment of the new activity baseline A1 and new activity threshold A1', no additional activity will be deemed to have occurred (and thus, no activity signal-induced rate increase will be initiated) until threshold A1' is exceeded by the average peak-to-peak value of the processed activity signal.

At time t5, the patient goes from walking to running (or from walking at a slow pace to walking at a faster pace, as another example). At time t6, it is determined that the calculated value of the processed activity signal exceeds current activity threshold A1', thereby initiating another increase in the pacing rate, e.g., by 10 bpm (FIG. 5(b)), the establishment of the now exceeded threshold A1' as the new activity baseline and of a higher level of activity as the new activity threshold A1" (FIG. 5(a)), and the restart of timer 22 (FIG. 5(b)). A similar set of events occurs each time the then-current activity threshold is exceeded. In this way, the patient is spared the possibility of prolonged rate increases resulting from false triggerings, but will be subjected to the appropriately higher stimulation rates when actual exercise or a change in exercise level is detected. Put another way, the patient will not experience repeated increases in stimulation rate as the signal level hovers about the same activity threshold, but instead a new higher threshold will be applied upon each rate increase.

At time t9, the patient stops running and again assumes a resting state (FIG. 5(f)). The cessation of activity is sensed and, at time t10, the calculated value of the processed activity signal has dropped to 25% of the last exceeded threshold A1' (FIG. 5(a)) which led to the previous double rate increase (initially 15 bpm and then another 10 bpm). In response, the fallback program is initiated for gradual reduction of the stimulation rate toward the base rate (FIG. 5(b)).

The foregoing discussion of FIG. 5 assumes rate control by the activity signal only. However, as shown in FIG. 5(c), the blood temperature responds to the onset of exercise at time t1 by dropping slightly and then rising until, at t3, it is at a value determinative of a pacing rate exceeding that of the activity signal-induced rate (FIG. 5(d)). Since t3 is within the timer period, the stimulation rate control is thenceforth dictated by the sensed blood temperature, commencing from the previously initiated rate increase of 15 bpm above the base rate (FIG. 5 (e)). The blood temperature rises to a steady state value during the first stage of exercise, which is reflected in the combined stimulation rate until time t6, when the aforementioned second activity signal-induced rate increase of 10 bpm occurs. That new stimulation rate is maintained until t8, when the blood temperature-induced rate surpasses this activity signal-induced increased rate within the restarted timer period (FIG. 5(d). The sensed blood temperature again assumes control of the pacing rate as the temperature continues to rise to a new steady state value during the second stage of exercise.

After the patient stops running at time t9, and this is recognized from the processed activity signal at t10, the combined stimulation rate begins a gradual drop under the control of the fallback program (FIG. 5(e)), as previously described. At that time, the blood temperature has begun to drop from its relatively high level, and at t11 the temperature commences to drop at a faster pace with a concomitant stimulation rate, but still somewhat slower than the rate according to the fallback program. The sensed blood temperature then again assumes control of the rate reduction toward the base rate. In this manner, it is assured that the pacing rate reduction meets the physiological requirements of the patient to the usual aftereffects of heavy exercise, including the body's demand for replenishment of depleted oxygen, which are better accommodated by rate control under the more gradual decrease of the blood temperature. If the patient had stopped exercising before the detected value of the blood temperature had assumed or reassumed control of pacing rate from the activity signal, the stimulation rate would have returned to the base rate strictly according to the fallback program instituted in response to the drop in calculated value of the processed activity signal. However, that would be compatible with the physiological needs of the patient because, in those circumstances, the exercise session would not have extended beyond the relatively short period set by the timer 22.

Figure 6:
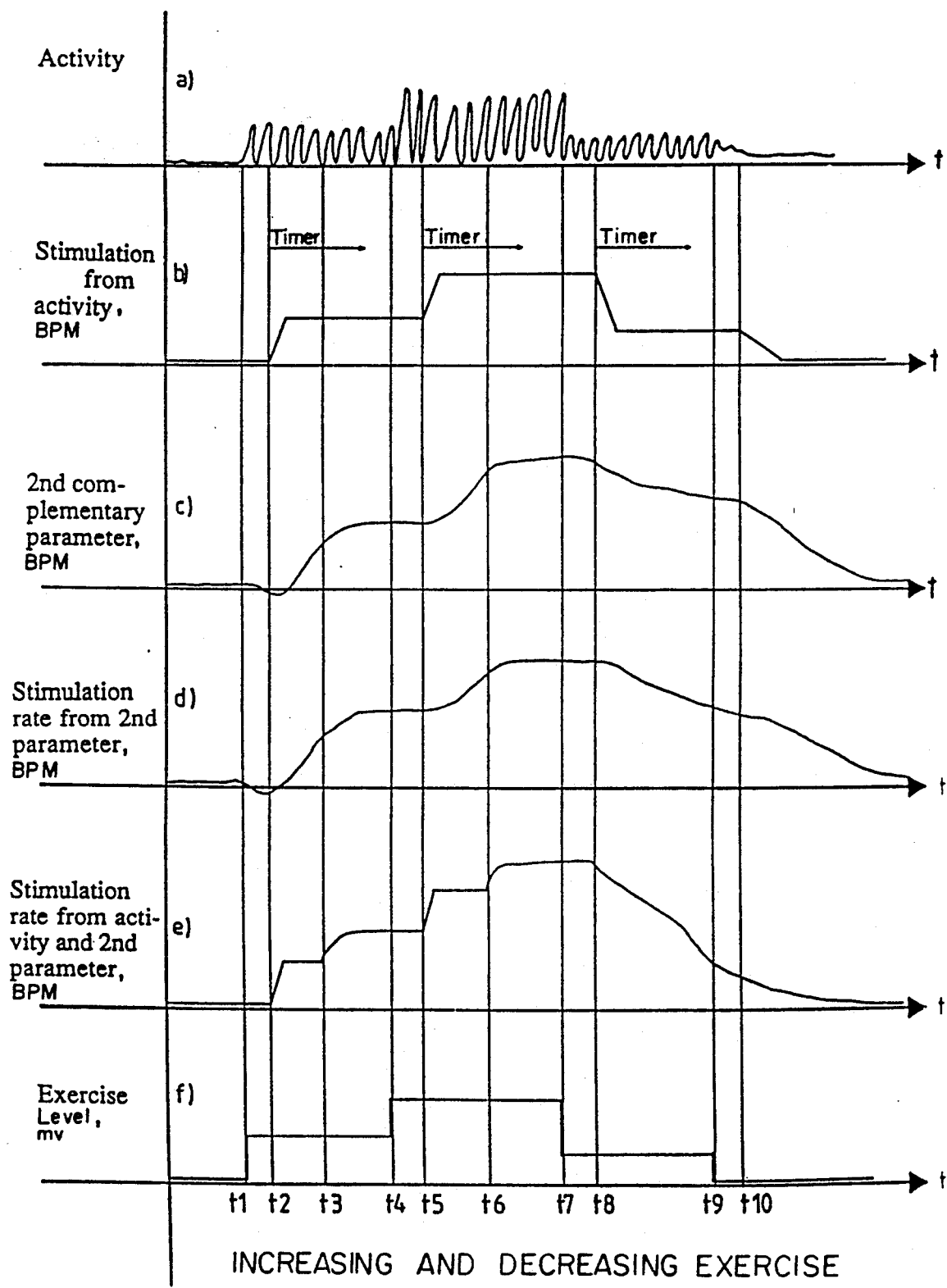

FIG. 6 provides another example of exercise with increasing workloads, and also with decreasing workloads, as shown in part (f) From the descriptions of FIGS. 3, 4 and 5, it will be apparent that an activity signal-induced rate increase takes place at time t2 (FIG. 6(e)) in response to commencement of patient exercise at time t1 which exceeds the initial activity threshold. The blood temperature-dictated stimulation rate takes control at time t3 and continues to t5, when the output of the activity sensor is recognized as indicative of additional exercise (because the new activity threshold was exceeded at t4), and the rate is increased. At t6, the rate determined from the blood temperature again assumes control.

At time t7, the level of exercise abruptly decreases, and is detected by the activity sensor, but exercise does not cease entirely and the calculated value of the processed activity signal remains higher than 25% of the last-exceeded activity threshold. Accordingly, the fallback program would not reduce the stimulation rate to the base rate, but only by an amount proportional to the decrease of the activity signal. That is, the reduction in heart rate (- HR) is a function of the decrease in activity (- activity), based on the activity level observed after the decrease. If, for example, the cumulative activity-induced rate increase up to time t6 was 25 bpm, and the activity at t8 is 40% of that at t6, the rate at t8 would be reduced by 15 bpm (i.e., 60% of 25 bpm) and would still remain 10 bpm above the base rate (FIG. 6(b)). In terms of the stimulation rate resulting from both the activity signal and the blood temperature value, the rate reduction begins at t8 under the fallback program until the point at which the blood temperature-induced rate takes over, followed by the impact of the next fallback program at t10, when the calculated value of the activity signal has dropped to 25% of the last-exceeded activity threshold FIG. 6(e)).

Figure 7:
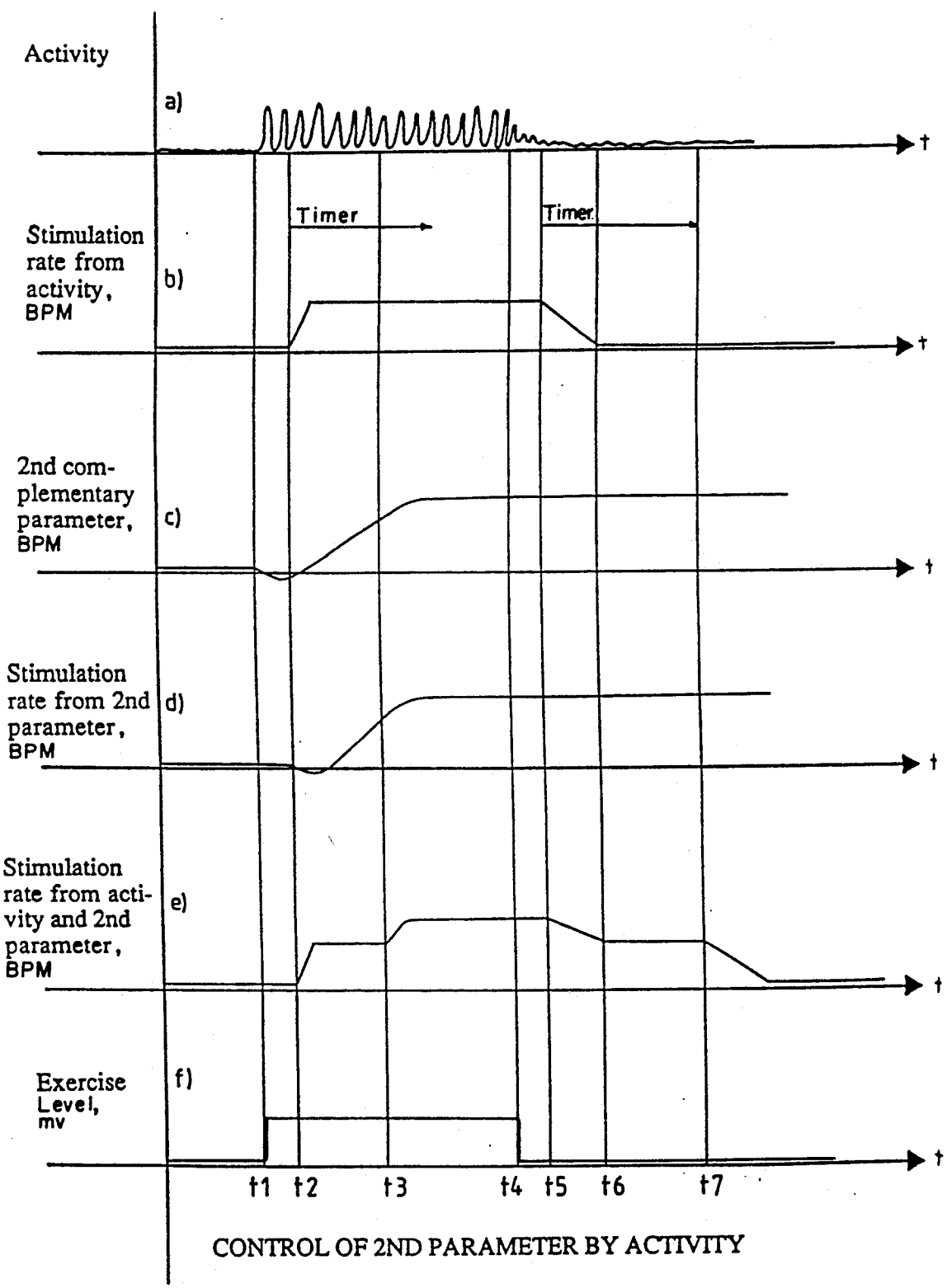

FIG. 7 reflects a situation in which the activity sensor detects exercise at t1 and a cessation of exercise at t4, corresponding to that of FIG. 4. Here, however, the sensed value of the blood temperature (or other slower reacting second complementary parameter) remains at a relatively high value (FIG. 7(c)), for example, because the patient has become feverish or because of defective measurement. At time t5, the timer 22 is started, commencing the running of the preset period, and the fallback program is initiated (FIG. 7(b)), as previously described. The stimulation rate is gradually reduced toward the base rate (FIG. 7(e)), but does not fully return to the base rate because of the contribution of the blood temperature-induced rate. However, for purposes of a rate decrease, both the absolute amplitude of the activity signal and the relative changes in amplitude thereof are determined and assessed with respect to the value of the second complementary parameter. From this, it is seen that at time t7 the absolute amplitude of the activity signal is less than a preselected minimum level, and therefore fails to confirm rate indicated by the blood temperature level. Accordingly, when the timer period expires, the fallback program resumes to reduce the rate to the predetermined base rate. As previously noted, the timer period is set according to the selection of the second complementary parameter and the sensitivity of that parameter to exercise. Thus, the use of two parameters in this manner permits control of stimulation rate without improper tachycardia despite a slow response, false triggering or an erroneous reading.

Figure 8:
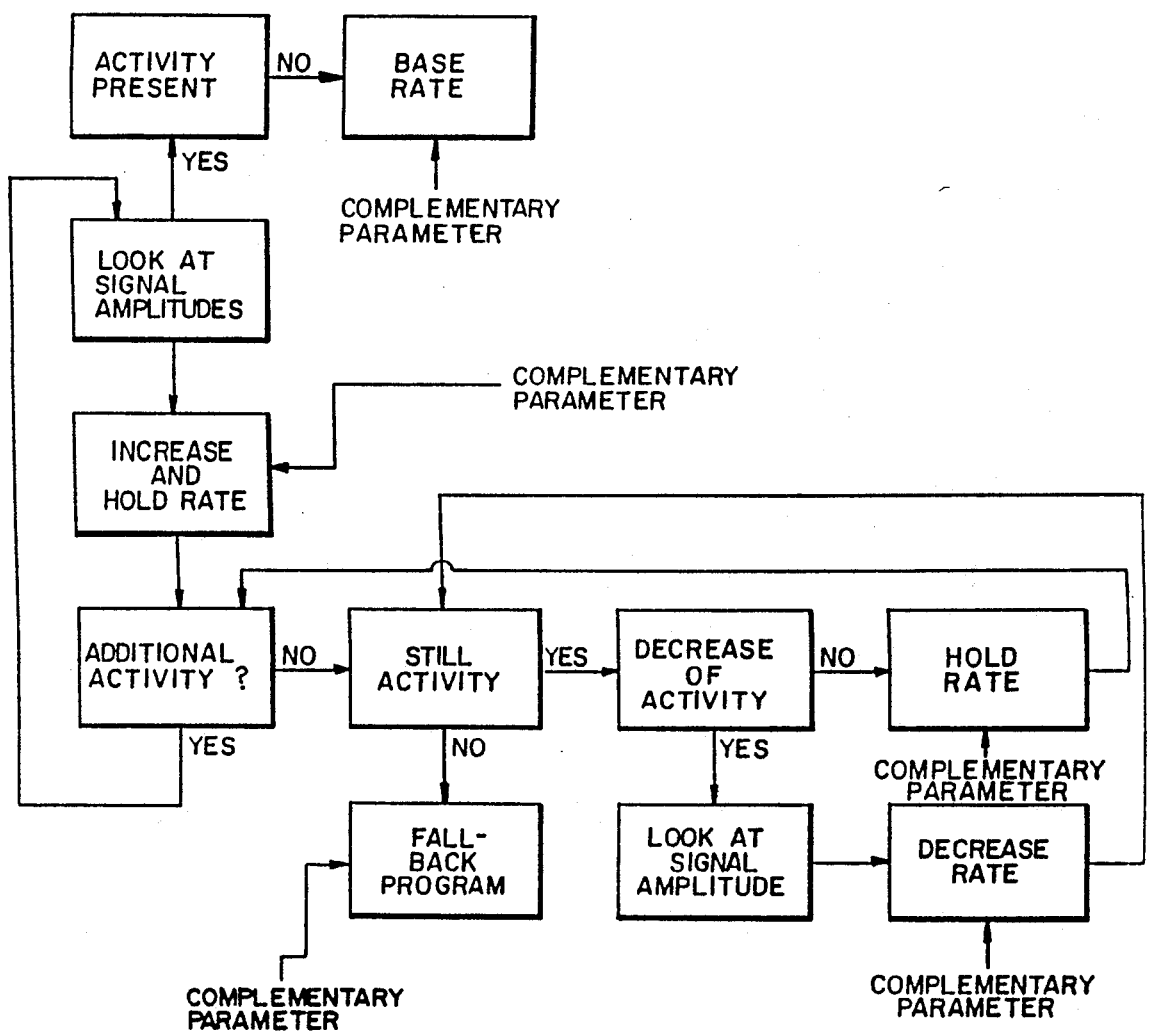
FIG. 8 is a flow chart of the functioning of the cardiac pacemaker of FIG. i and FIGS. 9a and 9b are respectively a front view and a cross-sectional view of one example of a mechanoelectrical transducer which could possibly be used in the pacemaker of FIG. 1.

FIG. 8 is a flow chart of the operation of a pacemaker according to the invention. If no activity is detected, the stimulation rate is held at the base rate, which may be influenced by the complementary parameter. If activity is detected, the maximum and minimum amplitudes of the filtered activity signal are evaluated, and if the current activity threshold is exceeded the stimulation rate is increased accordingly and is held at the increased rate. The timer is started at the instant of the increase, and the detected value of the complementary parameter is monitored to determine whether it will influence this rate. At the same time, the exceeded threshold becomes the new activity baseline and a higher activity threshold is established that must be exceeded for additional activity to be detected.

If the calculation of average maximum and minimum amplitudes of the activity signal from several samples taken over successive predetermined time intervals exceeds the new higher activity threshold, the stimulation rate is again increased and held, and the timer is restarted to establish the period within which the influence of the complementary parameter is assessed once again. This process continues with each determination that additional activity has occurred. The increase in stimulation rate is effected in steps which decrease in size with the higher instantaneous rates.

If the logic determines that there is no additional activity, the activity sensor output continues to be evaluated to assess whether there is ongoing exercise, and if there is none, the fallback program is commenced to reduce the rate toward the base rate, which again may be influenced by the second complementary parameter. If there is ongoing exercise without decreasing level, the rate is held until additional activity or a decrease in the exercise level is detected. If a decrease, the stimulation rate is decreased accordingly. If the calculation of the processed activity signal amplitude drops to 25% of the previously exceeded activity threshold, the stimulation rate is reduced to the base rate, but if the drop is less than 75% the reduction in rate is a function of the delta (i.e., the amount of the drop).

The cycle repeats itself with each detection of patient exercise (including any false triggerings as described earlier herein). After each new occurrence (e.g., onset of exercise, increase in exercise, decrease in exercise, cessation of exercise) the timer is restarted to establish a new period during which to assess the influence of the complementary parameter on rate control.

Figure 9A:
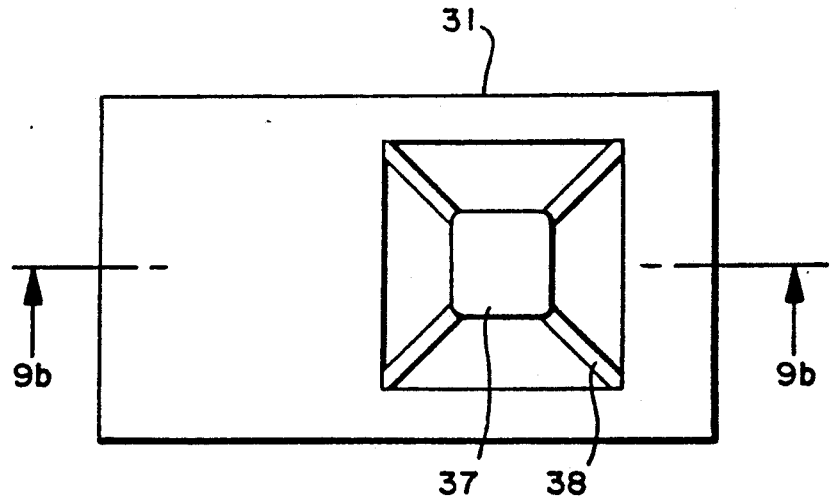
Figure 9B:
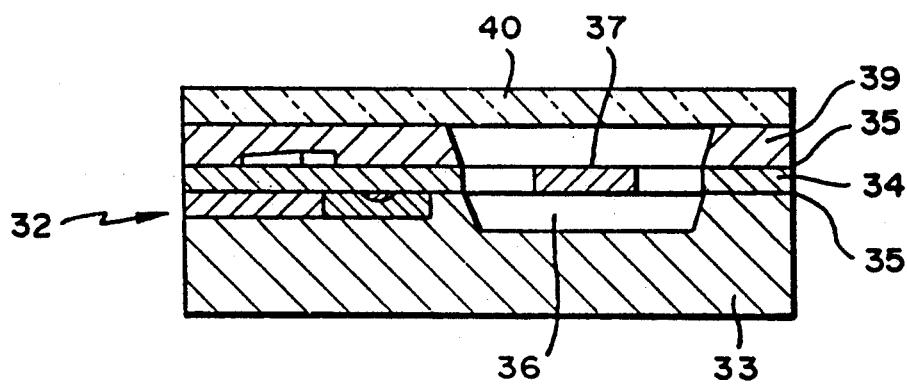

FIGS. 9a and 9b illustrate an exemplary embodiment of a mechanoelectrical transducer which might be used in the pacemaker of the invention, but is to be emphasized that any transducer having the characteristics described earlier herein may be employed satisfactorily as an activity sensor. Transducer 31 has an integrated signal filter circuit 32, to provide the proper frequency pass band. The unit 31 comprises a silicon monocrystalline substrate 33 with a 1-0-0 orientation of the crystal planes. A p+ epitaxial conductive layer is formed on the surface of the substrate, followed by a polycrystalline silicon layer 34 sandwiched between passivating layers 85 of silicon dioxide. By anisotropic etching, a cavity 36 is formed in the substrate 33, and portions of layers 34, 35 are removed to form a rectangular plate 37 connected by four arms 38 to the corners of cavity 36. The rectangular plate 37 with arms 38 forms the element responsive to acceleration. A further layer 39 is deposited on the structure, with an opening extending contiguous with the perimeter of cavity 36, to permit axial movement of the rectangular plate on the arms. Finally, a protective layer 40, e.g., a glass plate, is placed over the structure. The integrated circuit 32 for processing the signal generated by movement of the rectangular plate 37 via arms 38 may be fabricated in the silicon layers by conventional semiconductor integrated circuit process technology.

FIGS. 10a to 10d illustrate test results using a cardiac pacemaker according to the invention, in which central venous blood temperature of the patient was selected as the second complementary parameter. The tests were performed on a healthy person connected to (but not paced by an external pacemaker otherwise conforming to the principles of the present invention. The natural (intrinsic) heart rate $HR_{int}$ of the subject while undergoing exercise was recorded on a strip chart and compared to the similarly recorded stimulation rate $HR_{stim}$ generated by the pacemaker pulse generator as controlled by the control system of the present invention. The "paced heart rate" was detected at the lead connections of the pulse generator.

The upper three diagrams of each FIG. were recorded as a function of time in minutes. The lowermost diagram of each FIG. (i.e., below the upper three diagrams) is indicative of the exercise regimen performed by the subject, for which the other diagrams of the respective FIG. were obtained. The uppermost of the three diagrams of each FIG. indicates the measured output of the mechanoelectrical transducer stated in digitized representations from a computer in units g related to gravity (curve g) and the measured values from a blood temperature probe in $^\circ C$ (curve T). The middle diagram of each FIG. shows the heart rate $HR_g$ calculated from and according to the curve g, and $HR_T$ calculated from and according to the curve T, both heart rates being in units of bpm, as calculated independently of each other by the circuitry of the control system The lower of those three diagrams of each FIG. shows a curve of the intrinsic heart rate of the subject (curve $HR_{int}$), and the stimulation rate (curve $HR_{stim}$) as calculated by the control system of the present invention by combining the heart rates $HR_g$ and $HR_T$ according to the principles described above.

Figure 10A:
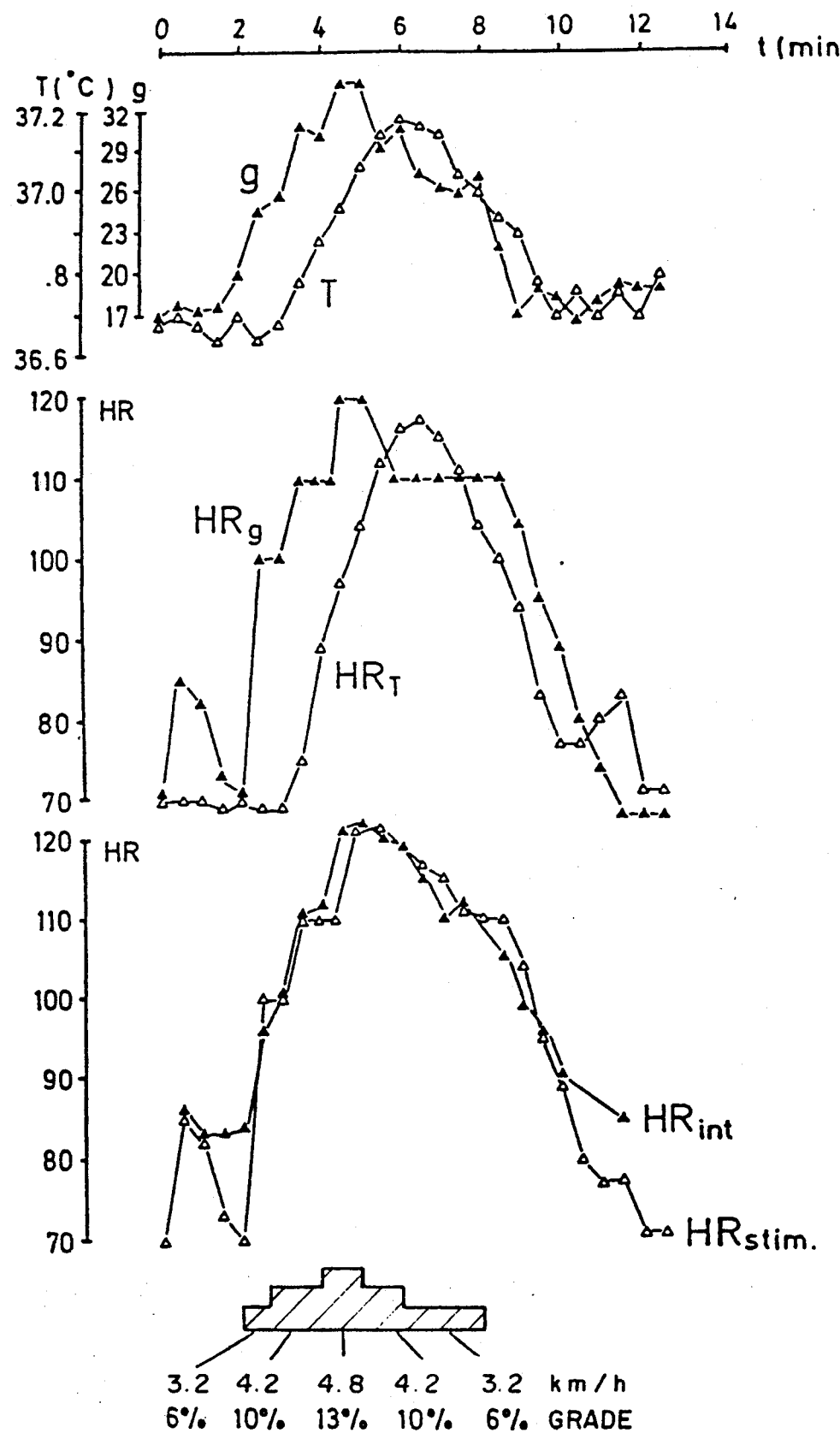

In FIG. 10a, the subject underwent a treadmill test in which he was subjected to different speeds and different inclines (grades) by the treadmill. It will be observed that the stimulation rate curve closely matches the natural heart rate curve virtually throughout the test regimen.

Figure 10B:
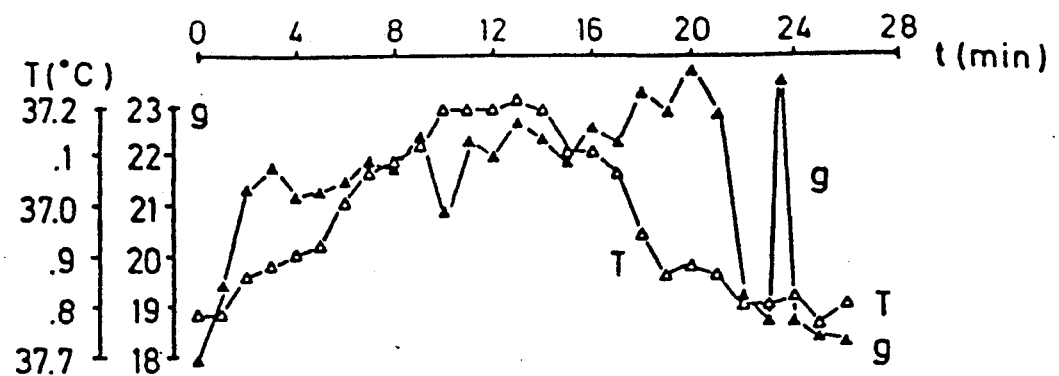
Figure 10B:
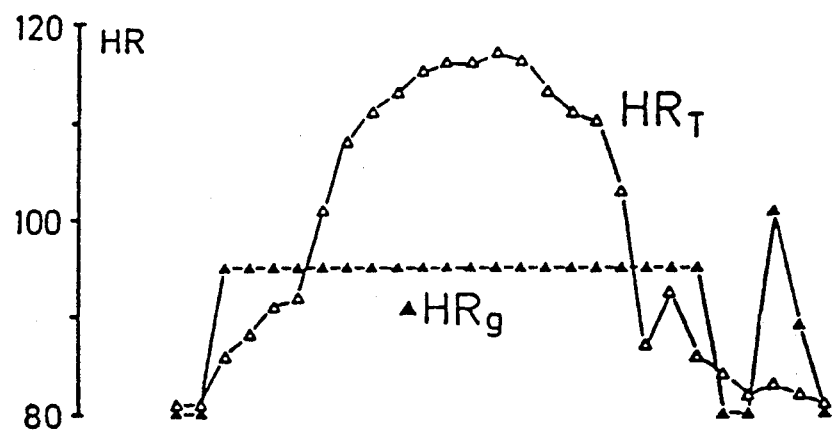
Figure 10B:
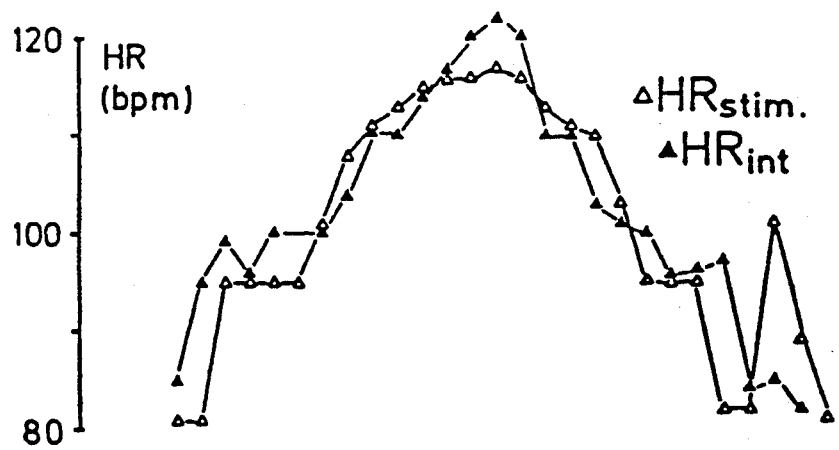
Figure 10B:
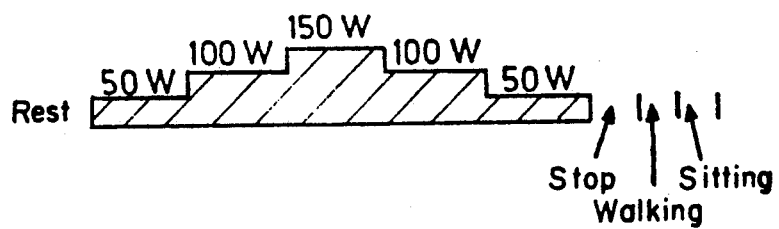

In FIG. 10b, the test subject underwent increasing and decreasing exercise on an exercise bicycle. It is interesting to note the increase in curve g in the interval from 16 to 20 minutes despite the decrease in the level of exercise, which is also apparent from the blood temperature curve T. This clearly shows that the test subject was tiring, and moved more on the bicycle notwithstanding that the metabolic expenditure was decreasing. Nevertheless, the curve of stimulation rate constituting a combination of the rates dictated by the activity signals and the sensed blood temperature values in the manner earlier mentioned herein, again closely corresponds to the curve of the subject's natural heart rate over time.

Figure 10C:
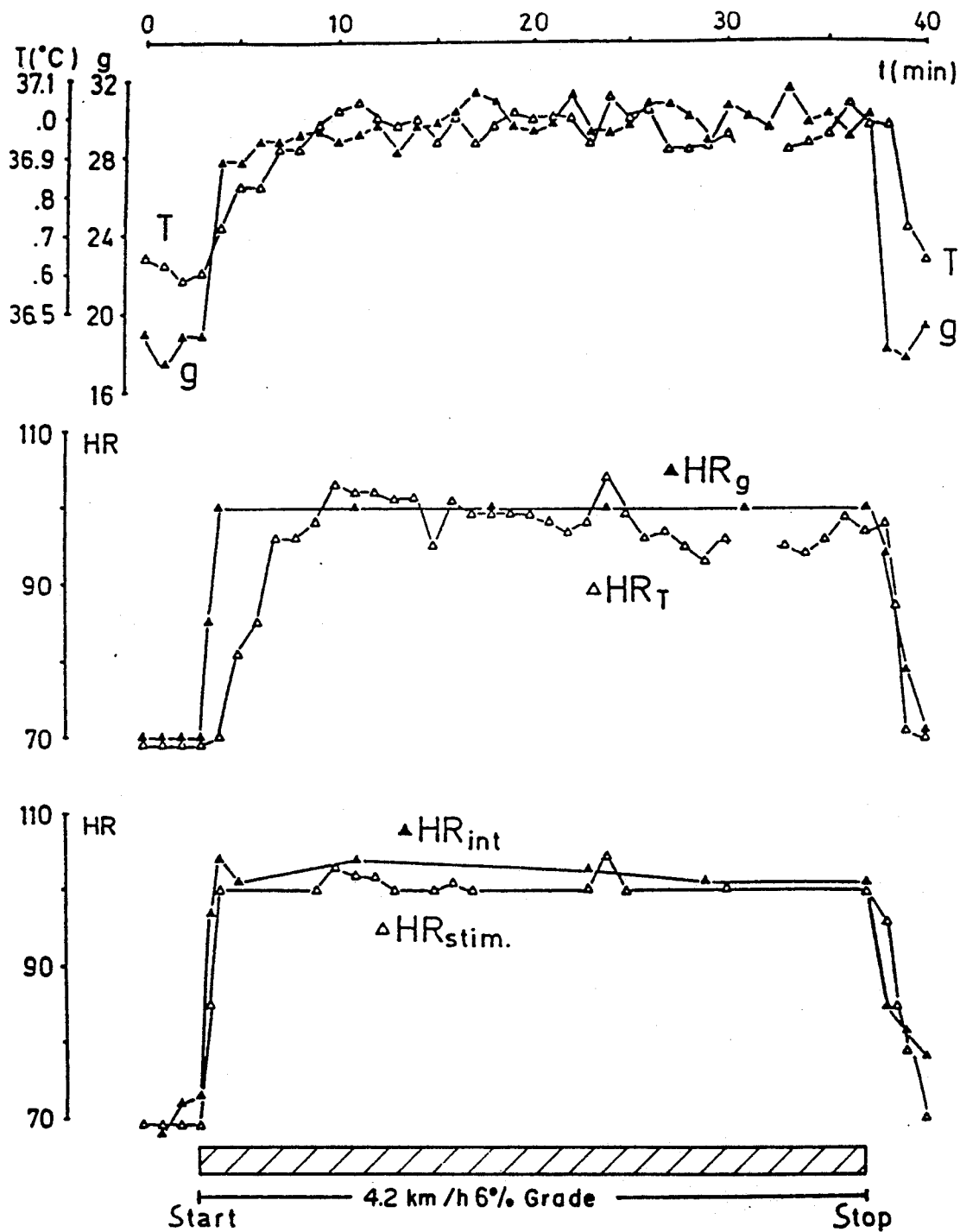

In FIG. 10c, the test subject walked continuously at a speed of 4.2 kilometers per hour on a treadmill with an upward grade of 6%, for a period of extended duration. At about 25 minutes, the heart rate derived from the detected central venous blood temperature values fell somewhat below the rate derived from the activity values, but the combination of these rates resulted in a stimulation rate curve which again closely approximated the subject's natural heart rate curve with time.

Figure 10D:
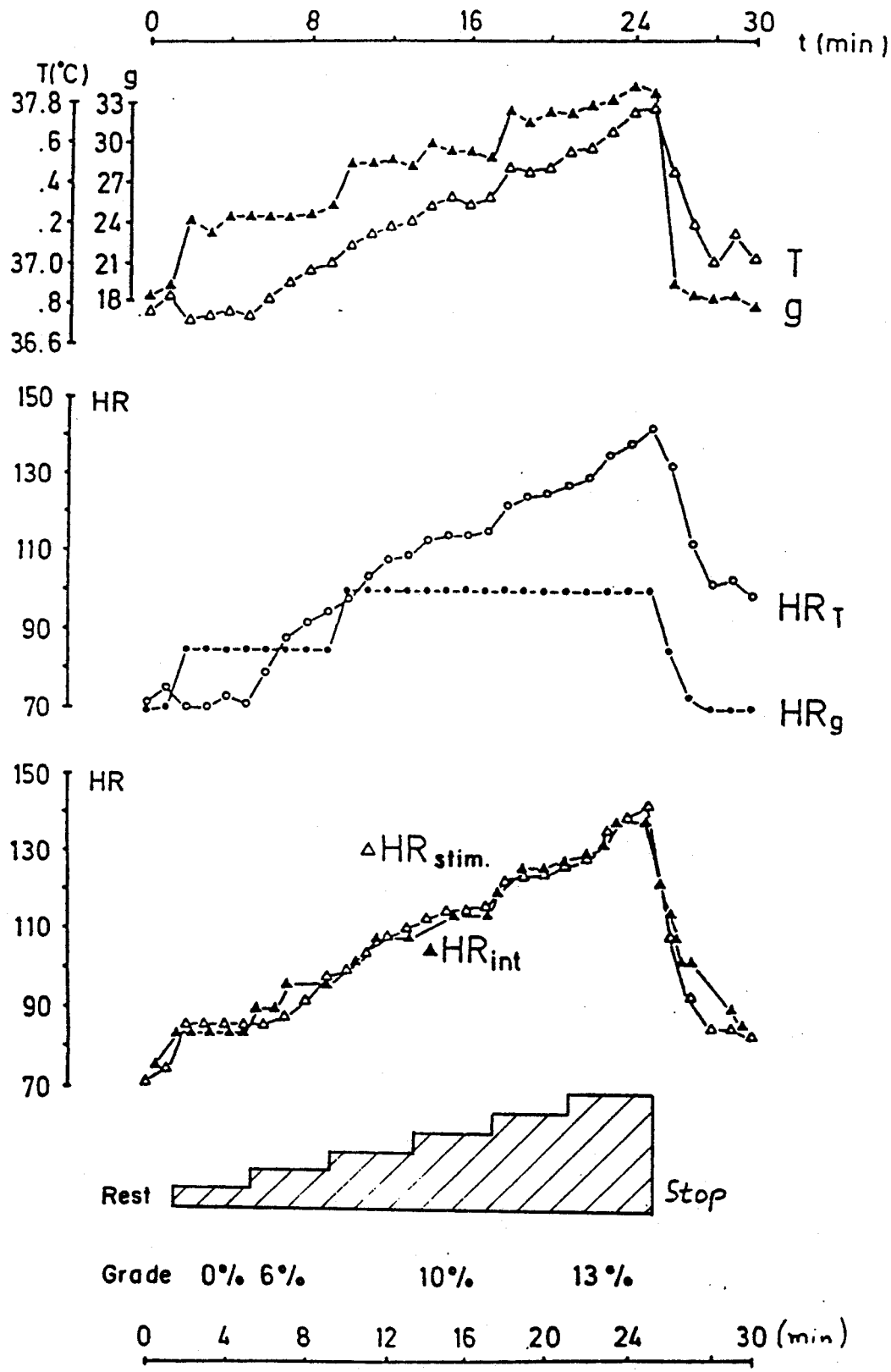

Finally, FIG. 10d shows the test results in which the subject underwent a treadmill test at increasing speeds and grades (constantly increasing workload), with a sudden cessation of exercise at the greatest speed and grade. As in FIG. 10b, the HR$_T$ curve was noticeably different from the HR$_g$ curve. In this test, the activity threshold values were exceeded twice. The determination of rate according to the activity signal is clearly observed at the onset, and the combined stimulation rate curve again closely duplicated the subject's natural heart rate curve over the test period.

While a preferred embodiment of the invention has been described, it will be apparent to those skilled in the art from consideration of the disclosure herein that various modifications may be implemented without departing from the inventive principles. Again, by way of example of modifications falling within the scope of the invention, the second parameter may be respiration, minute ventilation, stroke volume, blood oxygen saturation, blood pH balance, Q-T interval, or any of other known or contemplated parameter, or the time rate of change of any such parameter. Accordingly, it is intended that the invention be limited only by the appended claims.

What is claimed is:

1. An activity-sensing cardiac pacemaker for implantation in a patient, comprising
   a case housing at least a portion of the pacemaker,
   activity sensor means situated within said case for detecting movements of the patient, said activity sensor means including
   miniaturized accelerometer means integrated within hybrid electronic circuitry to distinguish between movements of the type which are attributable to physical exercise of the patient and movements of the type produced by spasmodic reaction to internal and external forces on the patient which are not attributable to physical exercise of the patient, for generating an electrical signal having a level representative of the level of physical exercise in which the patient is engaged,
   adjustable rate pulse generating means within said case for stimulating the patient's heart, and
   rate selecting means within said case, responsive to said electrical signal level, for adjusting the pulse rate of said pulse generating means to stimulate the patient's heart at a rate which is physiologically appropriate to the level of physical exercise of the patient.

2. The invention according to claim 1, wherein said accelerometer means has a frequency response characteristic limited to a range below 4 Hz to distinguish between patient movements during rhythmic physical exercise and patient movements produced by random internal and external forces on the patient which are not attributable to physical exercise.

3. The invention according to claim 2, wherein said accelerometer means is isolated from said case, whereby to respond to forces of acceleration of said case and to be substantially unresponsive to forces arising from static pressure on said case.

4. The invention according to claim 1, wherein, said pulse generating means and said rate selecting means are also integrated within said hybrid electronic circuitry.

5. The invention according to claim 4, wherein said hybrid electronic circuitry comprises a semiconductor device.

6. The invention according to claim 5, wherein said accelerometer means comprises a mechanoelectrical transducer having a natural frequency response characteristic limited to a range below 4 Hz.

7. The invention according to claim 5, wherein said accelerometer means is one of a piezoelectric, piezoresistive, or piezocapacitive device.

8. In an implantable activity-based cardiac pacemaker having a variable rate stimulus generator housed within a case, the improvement comprising
   an accelerometer housed within and isolated from said case for detecting forces of acceleration of said case and generating an electrical signal representative thereof,
   electrical circuit means for processing said signal to vary the rate of said stimulus generator according to the detected forces of acceleration of said case,
   said accelerometer and said circuit means being integrated together within electronic circuitry.

9. The improvement of claim 8, wherein said accelerometer includes a mechanoelectrical transducer having a natural frequency response characteristic limited to a range below 4 Hz.

10. The improvement of claim 8, wherein said circuit means includes an electrical filter having a frequency response characteristic limited to a range below 4 Hz.

11. The improvement of claim 8, wherein said electronic circuitry is fabricated in a semiconductor chip.

12. The improvement of claim 11, wherein said accelerometer is one of a piezoelectric, piezoresistive, or piezocapacitive device.

13. The improvement of claim 12, wherein said device has a natural frequency response characteristic limited to a range below 4 Hz.

14. In combination with an activity-sensing cardiac pacemaker for implantation in a patient, said pacemaker having a housing and adjustable rate pulse generating means and rate selecting means within said housing for adjusting the pulse rate of said pulse generating means to stimulate the patient's heart at a physiologically appropriate rate, the improvement comprising
    activity sensor means arranged and adapted to b e implanted in the patient to respond to movements of the patient for conversion thereof into a rate determining signal to be applied to said rate selecting means, said activity sensor means including miniaturized accelerometer means integrated within hybrid electronic circuitry for generating said rate determining signal.

15. The improvement of claim 14, wherein said activity sensor means is disposed within said housing.

16. The improvement of claim 14, wherein said accelerometer means has a frequency response characteristic selected to distinguish between patient movements during rhythmic physical exercise and patient movements produced by random internal and external forces unrelated to physical exercise, for converting said movements representative of physical exercise to an electrical output, and said hybrid electronic circuitry includes means responsive to said electrical output for generating said rate determining signal.

17. The improvement of claim 14, wherein said hybrid electronic circuitry comprises a semiconductor device.

18. The improvement of claim 14, wherein said accelerometer means comprises a transducer having a natural frequency response characteristic limited to a range below 4 Hz.

19. The improvement of claim 18, wherein said transducer is one of a piezoelectric, piezoresistive, or piezocapacitive device.

20. The improvement of claim 14, wherein said hybrid electronic circuitry includes an electrical filter having a frequency response characteristic limited to a range below 4 Hz.

* * * * *